United States Patent [19]

Sugimoto et al.

[11] Patent Number: 5,766,925
[45] Date of Patent: Jun. 16, 1998

[54] METHOD OF PRODUCING L-LYSINE

[75] Inventors: Masakazu Sugimoto; Yoshihiro Usuda; Tomoko Suzuki; Akiko Tanaka; Hiroshi Matsui, all of Kawasaki, Japan

[73] Assignee: Ajinomoto Co., Inc., Tokyo, Japan

[21] Appl. No.: 700,359

[22] PCT Filed: Feb. 23, 1995

[86] PCT No.: PCT/JP95/00268

§ 371 Date: Oct. 8, 1996

§ 102(e) Date: Oct. 8, 1996

[87] PCT Pub. No.: WO95/23864

PCT Pub. Date: Sep. 8, 1995

[30] Foreign Application Priority Data

Mar. 4, 1994 [JP] Japan ................ 6-035019

[51] Int. Cl.[6] ................ C12N 1/20; C12N 9/04
[52] U.S. Cl. ................ 435/252.32; 435/172.1; 435/190; 435/252.3; 536/23.2
[58] Field of Search ........... 435/252.3, 252.32, 435/190, 172.1; 536/23.2

[56] References Cited

U.S. PATENT DOCUMENTS

| | | | |
|---|---|---|---|
| 4,861,722 | 8/1989 | Sano et al. | 435/252.32 |
| 4,980,285 | 12/1990 | Sano et al. | 435/108 |
| 5,236,831 | 8/1993 | Katsumata et al. | 435/106 |
| 5,616,480 | 4/1997 | Sugimoto et al. | 435/172.3 |
| 5,641,660 | 6/1997 | Sinskey et al. | 435/115 |

FOREIGN PATENT DOCUMENTS

| | | |
|---|---|---|
| 0204326 | 12/1986 | European Pat. Off. |
| 09225 | 5/1993 | WIPO |

OTHER PUBLICATIONS

Katinka et al. (1980) Nucleotide sequence of the thrA gene of *Escherichi coli*. Proc. Natl. Acad. Sci. USA 77 (10): 5730–5733, Oct. 1980.

Zakin et al. (1983) Nucleotide sequence of the metL gene of *Escherichia coli*. J. Biol. Chem. 258 (5): 3028–3031, Mar. 1983.

Mateos et al. (1987) Nucleotide sequence of the homoserine dehydrogenase (thrA) of Brevibacterium lactofermentum. Nucleic Acids Research 15 (24): 10598, Dec. 1987.

*Primary Examiner*—Robert A. Wax
*Assistant Examiner*—Einar Stole
*Attorney, Agent, or Firm*—Oblon, Spivak, McClelland, Maier & Neustadt, P.C.

[57] ABSTRACT

A coryneform bacterium having high L-lysine productivity is provided by integrating a gene coding for aspartokinase originating from coryneform bacteria with desensitized feedback inhibition by L-lysine and L-threonine, into chromosomal DNA of a coryneform bacterium harboring leaky type homoserine dehydrogenase or a coryneform bacterium deficient in homoserine dehydrogenase gene.

30 Claims, 8 Drawing Sheets

```
                            *  *  *   *
            *    *           *  *  *  **
BL  MTSASAPSFNPGKGPGSAVGIALLGFGTVGTE    32
BS              MK----AIRVGLLGLGTVGSG   17
E1  VRVTHQMLFNTDQ----VIEVFVIGVGGVGGA    479
E2  IQGLHQSVFRAEK----RIGLVLFGKGNIGSR    471

*                        *
         *   *                         *      *
BL  VMRLMTEYGDELAHRIGGPLEVRGIA-VSDIS    63
BS  VVKIIQDHQDKLMHQVGCP--V-TIKKV----    42
E1  LLEQLKRQQSWLKNK---HIDLRVC-GVAN-S    506
E2  WLELFAREQSTLSAR---TGFEFVLAGVVD-S    499

*            *
BL  K------PREGVAPELLTEDAFALIEREDVDIV   90
BS  -------------LVKDLEKKREVDLPKEVLTT   62
E1  K-ALLTEVHGLNLENWQEELAQAKEPFNLGRL    537
E2  RRSLLSY-DGLDASRALAFFNDEAVEQDEESL    530

*
           * *                     * *
BL  VEVIGGIEYPRE-VVLAA--------------L   108
BS  E-VYDVIDDPDVDVVIEVIGGVEQTKQYLVDA    93
E1  IRLVKEYHLLN-PVIVNCTSSQAVADQYADFL    568
E2  F-LWMRAHPYDDLVVLDVTASQQLADQYLDFA    561
```

BL: BREVIBACTERIUM LACTOFERMENTUM    BS: BACILLUS SUBTILIS
E1: E. COLI HDI                      E2: E. COLI HDII
*: AMINO ACID COMMON TO THREE SECIES
**: AMINO ACID COMMON TO FOUR SECIES

*FIG. 2A*

```
              X   X X                              X
           X XXXXXXX   X               X          X  XX
    BL  - K A G K S V V T A N K - A L V A A H S A E - - L A D A A E A A    136
    BS  L R S K K H V V T A N K D L M A - - - - V Y G S E L L A E A K E    121
    E1  - R E G F H V V T P N K K A N T S S M D Y Y H Q L R Y A A E K S    599
    E2  - S H G F H V I S A N K L A G A S D S N K Y R Q I H D A F E K T    592

X           X         X                    X
           X X       X    X    X X  X       X       X   XX  X
    BL  N V D - L Y F E A A V A A A I P V V G P L R R S L - A G D Q I Q    166
    BS  N G C D I Y F E A S V A G G I P I L R T L E E G L S S - D R I T    152
    E1  R R K F L Y - D I N V G A G L P V I E N L Q N L L N A G D E L M    630
    E2  G R H W L Y - N A T V G A G L P I N H T V R D L I D S G D T I L    623

X X    X                                        X
           X X    X X     X         X                        X
    BL  S V M G I V N G T T N F I L D A M - D S T G A D Y A D S L A E A    197
    BS  K M M G I V N G T T N F I L T K M I K E K S P - Y E - - - - E V    179
    E1  K F S G I L S G S L S Y I F G K - L D E G M S - F S - - - - E A    656
    E2  S I S G I F S G T L S W L F L Q - F D G S V P - F T - - - - E L    649

X    X  XX     X    X    X        X    X X X
              X      X    XX    X       X    X   XXX    XXXX
    BL  T R - - - - L G Y A E A D P T A D V E G H D A A S K A A I L A S    225
    BS  L K E A Q D L G F A E A D P T S D V E G L D A A R K M A I L A R    211
    E1  T R L A R E M G Y T E P D P R D D L S G M D V A R K L L I L A R    688
    E2  V D Q A W Q Q G L T E P D P R D D L S G K D V S R K L V I L A R    681

BL: BREVIBACTERIUM LACTOFERMENTUM   BS: BACILLUS SUBTILIS
              E1: E. COLI HDI        E2: E. COLI HDII
              X: AMINO ACID COMMON TO THREE SPECIES
              XX: AMINO ACID COMMON TO FOUR SPECIES
```

*FIG. 2B*

```
            *
BL  IAFHTRVTADDVYCEGISNISAADIE-AAQQA      256
BS  L-GFSMNVDLEDVKVKGISQITDEDISF----      238
E1  ETGRELELADIEIEPVLPAEFNAEGDVAAFMA      720
E2  EAGYNIEPDQVRVESLVPA-HCEGGSIDHFFE      712

BL  GHTI--------------KLLAICEKFTNKEGKS    276
BS  ---------------SKRLGYTMKLIGIAQRDGSK   258
E1  NLSQLDDLFAARVAKARDEGKVLRYVGNIDED      752
E2  NGDELNEQMVQRLEAAREMGLVLRYVARFDAN      744

*         * *            *
        * *       * * *    *     * *
BL  AISARVHPTLLPVSHPLASVNKSFNAIFVEAE      308
BS  IE-VSVQPTLLPDHHPLSAVHNEFNAVYVYGE      289
E1  GV-CRVKIAEVDGNDPLFKVKNGENALAFYSH      783
E2  GK-ARVGVEAVREDHPLASLLPCDNVFAIESR      775

* * *      * *       *
          * * * *    * *    *   *
BL  AAGRLMFY--GNGAGGAPTASAVLGDVVGAAR      338
BS  AVGETMFY--GPGAGSMPTATSVVSDLVAVMK      319
E1  YYQPLPLVLRGYGAGNDVTAAGVFADLLRTLS      814
E2  WYRDNPLVIRGPGAGRDVTAGAIQSDINRLAQ      806

* *
BL  NKVHGGRAPGESTYANLPIADFGETTTRYHLD      370
BS  NMRLGVTGNSFVGPQYEKNMKSPSDIYAQQFL      351
E1  WK-LGV                                817
E2  L--L                                  806

BL  MD-VEDRVGVLAELASLFSEQGISLRTIRQEE      401
BS  RIHVKDEVGSFSKITSVFSERGVSFEKILQLP      383

BL  RDD---DARLIVVTHSALESDLSRTVELLKAK      430
BS  IKGHDELAEIVIVTHHTSEADFSDILQNLNDL      415

BL  PVVKAINSVIRLERD                       445
BS  EVVQEVKSTYRVEGNGWS                    433
```

*FIG. 3*

METHOD OF PRODUCING L-LYSINE

BACKGROUND OF THE INVENTION

The present invention relates to microbial industry, and in particular relates to a method of producing L-lysine by fermentation, and coryneform bacteria preferable for use in this production method.

L-lysine has been hitherto produced by fermentation using L-lysine-producing bacteria belonging to the genus Brevibacterium, Corynebacterium, Bacillus or Escherichia, which is synthesized in a biosynthesis system of any of these microorganisms from oxaloacetate through aspartate, aspartate β-aldehyde and so on. Various enzymes such as phosphoenol pyruvate carboxylase, aspartokinase and dihydrodipicolinate synthase participate in such an L-lysine biosynthesis pathway, however, many of these enzymes undergo feedback inhibition by L-lysine as a final product or by aspartic acid as an intermediate product. Thus when L-lysine is produced by fermentation, in order to improve the productivity, many mutant strains which do not undergo such inhibition are used.

For example, it is known that aspartokinase (hereinafter referred to as "AK") undergoes concerted inhibition by L-lysine and L-threonine synthesized in a branched pathway from the L-lysine synthesis pathway in coryneform bacteria belonging to the genera such as Brevibacterium and Corynebacterium. A mutant strain harboring AK which does not undergo the inhibition is used for L-lysine production (*J. Gen. Appl. Microbiol.*, 16, 373–391 (1970)).

A mutant strain, which lacks homoserine dehydrogenase (hereinafter referred to as "HD") considered to be an enzyme having the greatest influence on L-lysine productivity, is also used for production of L-lysine by fermentation. This is attributed to the fact that L-threonine is not synthesized due to deficiency in HD to catalyze a reaction for producing L-homoserine from aspartate β-semialdehyde as a first reaction in a synthesis pathway inherent to L-threonine branching from the L-lysine synthesis pathway through aspartate β-semialdehyde, resulting in progress of the L-lysine synthesis reaction without inhibition of the AK activity. As such an HD deficient strain, an HD completely deficient strain of *Corynebacterium glutamicum* is known (Nakayama, K. et al.; *J. Gen. Appl. Microbiol.* 7(3), 145–154 (1961)).

In addition to the HD completely deficient strain as described above, a mutant strain harboring so-called leaky type HD is considered to be effective for L-lysine production, as well. The HD completely deficient strain cannot synthesize L-threonine and L-methionine, and thus it cannot grow unless these amino acids are present in a medium. On the contrary, if an HD leaky type strain can be obtained that harbors a leaky type HD which does not substantially exhibit activity so much to suppress L-lysine production but has HD activity a little, it becomes possible to make growth without addition of L-threonine and L-methionine to a medium, and it becomes convenient to prepare the medium.

Additionally, the leaky type HD has small affinity to aspartate β-semialdehyde as its substrate. Therefore, the HD leaky type strain synthesizes a considerable amount of aspartate β-semialdehyde for synthesizing L-threonine, L-methionine and L-isoleucine required for the growth. Aspartate β-semialdehyde synthesized in a considerable amount is consequently converted into L-lysine.

On the other hand, the HD completely deficient strain is considered to be still useful in that it completely suppresses production of L-threonine in amount, however, the deficiency in HD as a result of mutation has a possibility to restore the activity due to reverse mutation. Thus an HD deficient strain, in which such a possibility is extremely low with a destroyed HD gene, is considered to be more useful. A nucleotide sequence of an HD gene has been reported by Peoples et al. for *Corynebacterium glutamicum* (Peoples, O. P. et al., *Molecular Microbiology*, 2(1), 63–72 (1988)).

Since the HD leaky type strain and the HD deficient strain do not produce L-threonine, AK does not undergo feedback inhibition. Accordingly, it is expected that if the AK gene is amplified in cells of the HD leaky type strain and the HD deficient strain, the L-lysine synthesis reaction proceeds, and the L-lysine productivity is improved. It is further expected that L-lysine productivity is more improved by introducing, into coryneform bacteria, mutation of AK to avoid feedback inhibition by L-lysine and L-threonine in combination with leakage or deficiency of HD.

DISCLOSURE OF THE INVENTION

The present invention has been made taking the aforementioned viewpoints into consideration, a task of which is to obtain an HD leaky type strain and an HD gene-destroyed strain, and provide an HD leaky type strain and an HD deficient strain with an amplified AK gene, and an HD leaky type strain and an HD gene-destroyed strain harboring AK which does not undergo feedback inhibition by L-lysine and L-threonine, in order to improve the L-lysine productivity of coryneform bacteria.

In order to solve the aforementioned task, the present inventors have obtained an HD leaky type mutant strain of *Brevibacterium lactofermentum*, isolated a wild type HD gene and a leaky type HD gene to clarify their structures, introduced the leaky type HD gene and a partially deleted HD gene into a wild strain of *Brevibacterium lactofermentum*, and thus created an L-lysine-producing strain having improved L-lysine productivity. The present inventors have succeeded in further improvement in L-lysine productivity by amplifying an AK gene in cells of the L-lysine-producing strain thus obtained, or by introducing a gene coding for AK which does not undergo feedback inhibition by L-lysine and L-threonine, and arrived at the present invention.

Namely, the present invention provides a DNA fragment which codes for homoserine dehydrogenase originating from a coryneform bacterium in which at least one of a 23rd leucine residue and a 104th valine residue as counted from its N-terminus is changed to another amino acid residue; a coryneform bacterium which harbors a gene coding for mutant homoserine dehydrogenase originating from a coryneform bacterium in which at least one of a 23rd leucine residue and a 104th valine residue as counted from its N-terminus is changed to another amino acid residue; and a coryneform bacterium which is transformed by integrating the aforementioned gene coding for mutant type homoserine dehydrogenase into chromosomal DNA by way of homologous recombination with a homoserine dehydrogenase gene on a chromosome of the coryneform bacterium.

In another aspect, the present invention provides a coryneform bacterium wherein its homoserine dehydrogenase gene is destroyed by integrating a DNA fragment coding for a part of homoserine dehydrogenase originating from a coryneform bacterium into chromosomal DNA by way of homologous recombination with a homoserine dehydrogenase gene on a chromosome of the coryneform bacterium. In still another aspect, the present invention provides a coryneform bacterium which harbors in its cells recombinant DNA constructed by ligating an aspartokinase gene originating from a coryneform bacterium with a vector autonomously replicable in cells of coryneform bacteria, and expresses no wild type homoserine dehydrogenase; and a coryneform bacterium which is transformed by integrating, into chromosomal DNA of the coryneform bacterium, a gene coding for aspartokinase originating from a coryneform bacterium with desensitized feedback inhibition by L-lysine and L-threonine, and expresses no wild type homoserine dehydrogenase. In still another aspect, the present invention provides a method of producing L-lysine comprising the steps of cultivating the coryneform bacterium described above in an appropriate medium, producing and accumulating L-lysine in a culture thereof, and collecting L-lysine from the culture.

In this specification, occasionally, a strain which produces wild type HD or wild type AK is referred to as "wild strain", HD having the leaky type mutation which scarcely exhibits substantial HD activity but has HD activity a little is merely referred to as "mutant type HD", AK having mutation not to undergo feedback inhibition by L-lysine and L-threonine is referred to as "mutant type AK", and a partially deleted HD gene is referred to as "deletion type HD gene". Further, the integration of recombinant DNA comprising a foreign HD gene or a foreign AK gene and a vector into chromosomal DNA by way of homologous recombination with an HD gene or an AK gene on host chromosomal DNA is referred to as "gene integration", and the achievement of a state in which the HD gene or the AK gene on the chromosome is replaced by the foreign HD gene or the foreign AK gene by allowing one copy of an HD gene or an AK gene to fall off together with the vector from a state in which the recombinant DNA is integrated into the chromosomal DNA is referred to as "gene replacement". Furthermore, a mutant strain harboring a mutant type HD gene or a strain subjected to gene replacement with a mutant type HD gene is merely referred to as "HD mutant strain", and a strain subjected to gene replacement with a partially deleted HD gene is referred to as "HD deficient strain", as well.

The coryneform bacteria referred to in the present invention is a group of microorganisms defined on page 599 in "Bergey's Manual of Determinative Bacteriology", eighth edition (1974), which reside in aerobic Gram-positive non-acid-fast rods having no spore-forming ability, including bacteria belonging to the genus Corynebacterium, bacteria belonging to the genus Brevibacterium having been hitherto classified into the genus Brevibacterium but united as bacteria belonging to the genus Corynebacterium at present, and bacteria belonging to the genus Brevibacterium closely relative to bacteria belonging to the genus Corynebacterium.

The HD mutant strain obtained according to the present invention is excellent in L-lysine productivity, and it can grow even when L-methionine and L-threonine, or L-homoserine is absent in a medium. The HD deficient strain of the present invention is excellent in L-lysine productivity because of no expression of the HD gene, and it can stably maintain this property.

Further, the HD mutant strain and the HD deficient strain with amplified AK gene, as well as the HD mutant strain and the HD deficient strain harboring the mutant type AK gene are more excellent in L-lysine productivity.

DETAILED DESCRIPTION OF THE INVENTION

The present invention will be explained in detail below.
<1> Preparation of leaky type HD mutant strain and mutant type HD gene A mutant strain which produces HD having leaky type mutation is obtained by performing a mutation treatment of a coryneform bacterium which produces wild type HD. For the mutation treatment of the coryneform bacterium, a treatment is conducted by using ultraviolet light irradiation or a mutating agent usually used for artificial mutation such as N-methyl-N'-nitro-N-nitrosoguanidine (NTG).

Bacterial cells after the mutation treatment were subjected to single colony isolation to select those producing the leaky type HD from each of colonies. Leaky type HD mutant strains can grow on a minimum medium, cannot grow on a minimum medium added with excessive L-methionine and L-threonine, but can grow on a minimum medium added with L-homoserine, or L-methionine and L-threonine. Thus they can be selected using the foregoing as a criterion (Shiio, I. & Sano, K., *J. G. A. M.*, 15, 267–287 (1969)). In order to confirm the fact that mutant strains thus obtained produce the leaky type HD, it is preferable to extract a crude enzyme solution from bacterial cells and compare the HD specific activity with that of wild type HD.

The enzyme activity of HD can be measured in accordance with, for example, a method of Kalinowski et al. (Kalinowski, J. et al., *Mol. Gen. Genet.*, 224, 317–324 (1990)) using a crude enzyme solution prepared from bacterial cells in accordance with a method of Follettie et al. (Follettie, M. T. et al., *Molecular Microbiology*, 2, 53–62 (1988)).

In order to isolate the mutant type HD gene from the obtained leaky type HD mutant strains, chromosomal DNA is prepared from the leaky type HD mutant strains in accordance with, for example, a method of Saito and Miura (H. Saito and K. Miura, *Biochem. Biophys. Acta*, 72, 619 (1963)), and the HD gene is amplified by means of a polymerase chain reaction method (PCR; see White, T. J. et al., *Trends Genet.*, 5, 185 (1989)). For DNA primers to be used for the amplification reaction, those complementary to both 3' terminals of a DNA double strand containing an entire or partial region of the HD gene are used. When only a partial region of the HD gene is amplified, it is necessary to screen a DNA fragment containing an entire region from a chromosomal DNA library using such DNA fragments as primers. When an entire region of the HD gene is amplified, a PCR reaction solution containing a DNA fragment including the amplified HD gene is subjected to agarose gel electrophoresis, followed by extraction of the objective DNA fragment. Thus the DNA fragment containing the HD gene can be recovered.

DNA primers may be appropriately prepared, for example, on the basis of a sequence known for *Corynebacterium glutamicum* (Peoples, O. P. et al. *Molecular Microbiology*, 2(1), 63–72 (1988)). Specifically, primers which can amplify a region comprising 1150 base pairs coding for the HD gene are preferable, and for example, two species of primers defined with SEQ ID NOS: 1 and 2 are suitable. The primer DNA can be synthesized in accordance with an ordinary method such as a phosphoamidite method (see *Tetrahedron Letters*, 22, 1859 (1981)) by using a commercially available DNA synthesizer (for example, DNA Synthesizer Model 380B produced by Applied Biosystems). Further, the PCR can be performed by using a commercially available PCR apparatus (for example, DNA Thermal Cycler Model PJ2000 produced by Takara Shuzo Co., Ltd.), using Taq DNA polymerase (supplied by Takara Shuzo Co.,Ltd.) in accordance with a method designated by the supplier.

It is preferable for the mutant type HD gene amplified by the PCR method to be connected to vector DNA autonomously replicable in cells of *Escherichia coli* (hereinafter referred to as "*E. coli*", as well) and/or coryneform bacteria to prepare recombinant DNA which is introduced into *E. coli* cells, in order to facilitate following operations. The vector autonomously replicable in cells of *E. coli* is preferably a plasmid vector, preferably as those autonomously replicable in cells of a host, including, for example, pUC19, pUC18, pBR322, pHSG299, pHSG399, pHSG398, and RSF1010.

It is preferable that such a vector is inserted with a DNA fragment having an ability to make the plasmid autonomously replicable in coryneform bacteria which can be prepared, for example, from plasmids pAM330 (see Japanese Patent Laid-open No. 58-67699), pHM1519 (see Japanese Patent Laid-open No. 58-77895), pCG1 (see Japanese Patent Laid-open No. 57-134500), pCG2 (see Japanese Patent Laid-open No. 58-35197), pCG4 (see Japanese Patent Laid-open No. 57-183799), and pCG11 (see Japanese Patent Laid-open No. 57-183799). Thus the vector can be used as so-called shuttle vector which is autonomously replicable in both of *E. coli* and coryneform bacteria.

Such a shuttle vector is exemplified by the followings. Microorganisms harboring each of the vectors and deposition numbers of international deposition institutes are indicated in parentheses.

pAJ655: *Escherichia coli* AJ11882 (FERM BP-136) *Corynebacterium glutamicum* SR8201 (ATCC 39135)

pAJ1844: *Escherichia coli* AJ11883 (FERM BP-137) *Corynebacterium glutamicum* SR8202 (ATCC 39136)

pAJ611: *Escherichia coli* AJ11884 (FERM BP-138)

pAJ3148: *Corynebacterium glutamicum* SR8203 (ATCC 39137)

pAJ440: *Bacillus subtilis* AJ11901 (FERM BP-140)

These vectors are obtained from deposited microorganisms as follows. Cells collected at the logarithmic growth phase are lysed with lysozyme and SDS to give a lysate from which a supernatant solution is obtained by centrifugation at 30,000×g. Polyethylene glycol is added to the supernatant solution to perform fractional purification by means of cesium chloride-ethidium bromide equilibrium density gradient centrifugation.

In order to introduce a plasmid into *E. coli* for transformation, it is possible to use, for example, a method of D. M. Morrison (*Methods in Enzymology*, 68, 326 (1979)), or a method for treating recipient cells with calcium chloride to increase permeability of DNA (Mandel, M. and Higa, A., *J. Mol. Biol.*, 53, 159 (1970)).

When the mutant type HD gene is isolated from the leaky type HD mutant strain, it is also obtained by preparing a chromosomal DNA library from the leaky type HD mutant strain using a plasmid vector or the like, selecting a strain harboring the mutant type HD gene from the library, and recovering recombinant DNA with the inserted mutant type HD gene from the selected strain. An example of a method for preparing the chromosomal library and selecting the strain harboring the mutant type HD gene from the library will be described below.

At first, a leaky type HD mutant strain is cultivated to obtain a culture. Any medium in which coryneform bacteria can grow is available for use. When L-threonine and L-methionine are contained in the medium in small amounts, it is preferable to add L-threonine and L-methionine, or L-homoserine beforehand. Next, bacterial cells are obtained by centrifuging the culture. Chromosomal DNA is obtained from the bacterial cells in accordance with, for example, a method of Saito and Miura (*Biochem. Biophys. Acta*, 72, 619 (1963)) or a method of K. S. Kirby (*Biochem. J.*, 64, 405 (1956)).

In order to isolate the mutant type HD gene from the chromosomal DNA thus obtained, a chromosomal DNA library is prepared. At first, the chromosomal DNA is partially decomposed with an appropriate restriction enzyme to obtain a mixture of various fragments. A wide variety of restriction enzymes can be used by controlling the degree of cutting by controlling a period of time of the cutting reaction or the like. For example, Sau3AI is allowed to act on the chromosomal DNA to digest it at a temperature of not less than 30° C., preferably at 37° C. at an enzyme concentration of 1–10 units/ml for various periods of time (1 minute to 2 hours).

Subsequently, the cut chromosomal DNA fragments are ligated with a vector autonomously replicable in *E. coli* cells to prepare recombinant DNA. Specifically, a restriction enzyme, which generates the same terminal nucleotide sequence as that by the restriction enzyme Sau3AI used for cutting the chromosomal DNA, for example, BamHI is allowed to act on the vector DNA to completely digest it under conditions of a temperature of not less than 30° C. and an enzyme concentration of 1–100 units/ml for not less than 1 hour, preferably for 1–3 hours, to achieve cutting and cleavage. Next, the chromosomal DNA fragment mixture obtained as described above is mixed with the cleaved and cut vector DNA, on which DNA ligase, preferably T4 DNA ligase is allowed to act under conditions of a temperature of 4°–16° C. and an enzyme concentration of 1–100 units/ml for not less than 1 hour, preferably for 6–24 hours, to obtain recombinant DNA.

Using the obtained recombinant DNA, for example, *E. coli* K-12 strain is transformed to prepare a chromosomal DNA library. The transformation may be performed by, for example, a method of D. M. Morrison (*Methods in Enzymology*, 68, 326 (1979)), or a method for treating recipient cells with calcium chloride to increase permeability of DNA (Mandel, M. and Higa, A., *J. Mol. Biol.*, 53, 159 (1970)).

In order to select a transformant strain harboring the mutant type HD gene from the obtained chromosomal DNA library, for example, an oligonucleotide probe may be synthesized on the basis of a sequence known for *Corynebacterium glutamicum* (Peoples, O. P. et al., *Molecular Microbiology*, 2(1), 63–72 (1988)), to perform colony hybridization using it. It is known that two kinds of *E. coli* HD genes (HD-1, HD-2) are present (Zakin, M. M. et al., *J. B. C.*, 258, 3028–3031 (1983)), however, any of them has no region corresponding to about 100 amino acid residues on the C-terminal side of *Corynebacterium glutamicum* HD. Thus when a sequence to be used for the probe is selected from this region, it does not hybridize to the HD gene on *E. coli* chromosome, which is preferable. Recombinant DNA containing the mutant type HD gene can be isolated from transformed strains thus selected in accordance with, for example, a method of P. Guerry et al. (*J. Bacteriol.*, 116, 1064 (1973)) or a method of D. B. Clewell (*J. Bacteriol.*, 110, 667 (1972)).

Alternatively, a strain which produces the leaky type HD may be created by using a wild type HD gene cloned from a coryneform bacterium in the same manner as described above. At first, DNA containing a wild type HD gene or an HD gene having another mutation is subjected to an in vitro mutation treatment, and DNA after the mutation treatment is ligated with vector DNA adapted to a host to obtain recombinant DNA. The recombinant DNA is introduced into a host microorganism to obtain transformants, and one which expresses the leaky type HD is selected from the transformants. Alternatively, it is also available that DNA containing a wild type HD gene or an HD gene having another mutation is ligated with vector DNA adapted to a host to obtain recombinant DNA, thereafter the recombinant DNA is subjected to an in vitro mutation treatment, the recombinant DNA after the mutation treatment is introduced into a host microorganism to obtain transformants, and one which expresses the leaky type HD is selected from the transformants.

The agent for performing the in vitro mutation treatment of DNA is exemplified by hydroxylamine. Hydroxylamine is a treatment agent for chemical mutation which causes mutation from cytosine to thymine by changing cytosine to $N^4$-hydroxycytosine.

The mutant type HD gene for use in the present invention is not especially limited provided that it codes for the leaky type HD, for which there are exemplified genes coding for HD having any of mutations in an amino acid sequence of wild type HD, including:

(1) mutation to change a 23rd leucine residue from the N-terminal to an amino acid residue other than the leucine residue;

(2) mutation to change a 104th valine residue from the N-terminal to an amino acid residue other than the valine residue; and (3) mutation to change the 23rd leucine residue from the N-terminal to an amino acid residue other than the leucine residue, and the 104th valine residue from the N-terminal to an amino acid residue other than the valine residue.

The amino acid sequence of wild type HD is herein specifically exemplified by an amino acid sequence of HD originating from a wild type strain of *Brevibacterium lactofermentum* shown in SEQ ID NO: 3 and SEQ ID NO: 4 in Sequence Listing.

With respect to the mutations described in the foregoing (1) to (3), mutation to change to a phenylalanine residue is exemplified for the 23rd leucine residue, and mutation to change to an isoleucine residue is exemplified for the 104th valine residue.

Any codon corresponding to the replaced amino acid residue is available especially regardless of its type provided that it codes for the amino acid residue. The amino acid sequence of harbored wild type HD may slightly differ depending on difference in bacterial species and bacterial strains. HD having such replacement, deletion or insertion of amino acid residues at positions irrelevant to the activity of the enzyme can be also used for the present invention.

For example, as will be described in Examples below, as a result of comparison of an amino acid sequence of HD originating from *Brevibacterium lactofermentum* 2256 strain (ATCC 13869) with an amino acid sequence reported for HD of *Corynebacterium glutamicum* (Peoples, O. P. et al., *Molecular Microbiology*, 2(1), 63–72 (1988)), it has been clarified that a 148th amino acid residue from the N-terminal is a glycine residue in HD of *Corynebacterium glutamicum*, while it is an alanine residue in HD of *Brevibacterium lactofermentum*. It is expected that the leaky type HD is obtained by introducing any of the aforementioned mutations (1) to (3) even in the case of HD of *Corynebacterium glutamicum* as described above.

<2> Preparation of wild type AK gene and mutant type AK gene

The wild type AK gene for use in the present invention can be prepared from wild strains of coryneform bacteria. A gene, which codes for AK in which cumulative feedback inhibition by L-lysine and L-threonine is substantially desensitized, can be prepared from a mutant strain in which cumulative feedback inhibition to the AK activity by L-lysine and L-threonine is substantially desensitized. Such a mutant strain can be obtained from a group of cells having been subjected to a mutation treatment applied to, for example, a wild strain of coryneform bacteria by using an ordinary mutation treatment method such as ultraviolet light irradiation or a treatment with a mutating agent such as N-methyl-N'-nitro-N-nitrosoguanidine (NTG). For measuring the AK activity, it is possible to use a method described by Miyajima, R. et al. in *The Journal of Biochemistry* (1968), 63(2), 139–148.

With respect to donor bacteria for the AK gene, a wild strain ATCC 13869 of *Brevibacterium lactofermentum*, and an L-lysine-producing bacterium AJ3463 (FERM P-1987) derived from the ATCC 13869 strain by a mutation treatment are most preferable donor bacteria.

In order to isolate the AK gene from the coryneform bacteria, chromosomal DNA is prepared in accordance with, for example, a method of Saito and Miura (H. Saito and K. Miura, *Biochem. Biophys. Acta*, 72, 619 (1963)), and the AK gene is amplified by means of a polymerase chain reaction method (PCR; see White, T. J. et al., *Trends Genet.*, 5, 185 (1989)).

For DNA primers to be used for the amplification, those complementary to both 3' terminals of a DNA double strand containing an entire or partial region of the AK gene are used. When only a partial region of the AK gene is amplified, it is necessary to perform screening by amplifying a DNA fragment containing an entire region from a gene library using DNA fragments of the region as primers. When an entire region is amplified, the DNA fragment is subjected to agarose gel electrophoresis, followed by excision of an objective band. Thus the DNA fragment containing the AK gene can be recovered.

For DNA primers, single strand DNA's of 23 mer and 21 mer represented by 5'-TCGCGAAGTAGCACCTGTCACTT-3' (SEQ ID NO: 5 in Sequence Listing) and 5'-ACGGAATTCAATCTTACGGCC-3' (SEQ ID NO: 6 in Sequence Listing) are most suitable to amplify a region of about 1643 bp based on, for example, a sequence known for *Corynebacterium glutamicum* (see *Molecular Microbiology* (1991), 5(5), 1197–1204; *Mol. Gen. Genet.* (1990), 224, 317–324). The DNA can be synthesized in accordance with an ordinary method using a phosphoamidite method (see *Tetrahedron Letters* (1981), 22, 1859) by using a DNA synthesizer Model 380B produced by Applied Biosystems. The PCR can be performed by using DNA Thermal Cycler Model PJ2000 produced by Takara Shuzo Co., Ltd., using Taq DNA polymerase in accordance with a method designated by the supplier.

It is preferable for the mutant type AK gene amplified by the PCR method to be connected to vector DNA autonomously replicable in cells of *E. coli* and/or coryneform bacteria to prepare recombinant DNA which is introduced into *E. coli* cells, in order to facilitate following operations. The vector autonomously replicable in cells of *E. coli* is preferably a plasmid vector, preferably as those autonomously replicable in cells of a host, including, for example, pUC19, pUC18, pBR322, pHSG299, pHSG399, pHSG398, and RSF1010.

When these vectors are inserted with a DNA fragment having an ability to make the plasmid autonomously replicable in coryneform bacteria, they can be used as so-called shuttle vectors which are autonomously replicable in both of *E. coli* and coryneform bacteria. In order to introduce a plasmid into *E. coli* for transformation, it is possible to use, for example, a method of D. M. Morrison (*Methods in Enzymology*, 68, 326 (1979)), or a method for treating recipient cells with calcium chloride to increase permeability of DNA (Mandel, M. and Higa, A., *J. Mol. Biol.*, 53, 159 (1970)).

The wild type AK gene is obtained by isolating the AK gene from the AK wild strain as described above, and the mutant type AK gene is obtained by isolating the AK gene from the AK mutant strain.

The mutant type AK gene to be used for the present invention is not especially limited provided that it codes for AK in which cumulative feedback inhibition by L-lysine and L-threonine is desensitized. However, its mutation may be exemplified, with respect to the amino acid sequence of the wild type AK, such that a 279th alanine residue from the N-terminal is changed to an amino acid residue other than alanine and other than acidic amino acids in α-subunit, and a 30th alanine residue is changed to an amino acid residue other than alanine and other than acidic amino acids in β-subunit. The amino acid sequence of the wild type AK is herein specifically exemplified by an amino acid sequence defined in SEQ ID NO: 9 in Sequence Listing for the α-subunit, and an amino acid sequence defined in SEQ ID NO: 11 in Sequence Listing for the β-subunit.

The aforementioned amino acid residue other than alanine and other than acidic amino acids is exemplified by threonine, arginine, cysteine, phenylalanine, proline, serine, tyrosine and valine residues.

Any codon corresponding to the amino acid residue to be replaced is available especially regardless of its type provided that it codes for the amino acid residue. It is postulated that the amino acid sequence of harbored wild type AK may slightly differ depending on difference in bacterial species and bacterial strains. AK having such replacement, deletion or insertion of amino acid residues at positions irrelevant to the activity of the enzyme can be also used for the present invention.

<3> Preparation of HD mutant strain and HD deficient strain

The HD mutant strain is obtained as described in <1> by performing a treatment of a coryneform bacterium which produces wild type HD with ultraviolet light irradiation or a mutating agent, and selecting a strain which produces mutant type HD from bacterial cells subjected to the mutation treatment. The HD mutant strain which expresses no wild type HD is also obtained by introducing a mutant type HD gene isolated from the HD mutant strain thus obtained into cells of a wild type coryneform bacterium, and performing gene replacement by way of homologous recombination with an HD gene on chromosome.

The mutant type HD gene may be replaced with the HD gene on the host chromosome as follows (see FIG. 1). Namely, a temperature-sensitive replication origin originating from *Brevibacterium lactofermentum*, the mutant type HD gene, and a marker gene for exhibiting resistance to a drug such as chloramphenicol are inserted into a plasmid vector to prepare recombinant DNA. The recombinant DNA is used to transform a coryneform bacterium, transformed strains are cultivated at a temperature at which the temperature-sensitive replication origin does not operate, and then they are cultivated in a medium containing the drug. Thus a transformed strain, in which the recombinant DNA is integrated into chromosomal DNA, is obtained.

The strain with the recombinant DNA integrated into the chromosome causes recombination with an HD gene sequence originally existing on the chromosome, in which two fused genes of the chromosomal HD gene and the mutant type HD gene are inserted into the chromosome in a state of interposing other portions of the recombinant DNA (vector portion, temperature-sensitive replication origin, and drug resistance marker). Therefore, the wild type HD is dominant in this state, and thus equivalent growth to that of the wild strain is exhibited in a minimum medium.

Next, in order to allow only the mutant type HD gene to remain on the chromosomal DNA, one copy of an HD gene is allowed to fall off together with the vector portion (including the temperature-sensitive replication origin and the drug resistance marker) by recombination of the two HD genes. For example, the strain with the integration on the chromosome is cultivated, and cultivated bacterial cells are spread and cultivated on a solid plate medium containing no drug. Grown colonies are replicated and cultivated on a solid plate medium containing the drug, and drug-sensitive strains are obtained. The fact that the vector portion falls off from chromosomes of the obtained drug-sensitive strains is confirmed by Southern hybridization, and the fact that the mutant type HD is expressed is confirmed.

When the gene replacement is performed by using an HD gene coding for a part of HD, that is a partially deleted HD gene, instead of the aforementioned mutant type HD gene, an HD deficient strain in which its chromosomal HD gene is replaced with the partially deleted HD gene is obtained.

As described in Example 1 below, it is postulated that a region on the N-terminal side in HD participates in the activity. Therefore, the site to be deleted in the HD gene is exemplified by a region on the N-terminal side, for example, a region within 350 amino acids, for example, a region of 100th to 200th amino acids or 250th to 350th amino acids from the N-terminal. Since the HD gene is located in the same operon as that of homoserine kinase existing downstream therefrom, it is preferable that the promoter site of the HD gene is not deleted so as not to inhibit expression of homoserine kinase.

Introduction of the recombinant DNA into cells of coryneform bacteria is possible by using a method in which recipient cells are treated with calcium chloride to increase permeability of DNA as reported for *E. coli* K-12 (Mandel, M. and Higa, A., *J. Mol. Biol.*, 53, 159 (1970)), or a method in which introduction is performed in a growth stage so that cells can incorporate DNA (so-called competent cells) as reported for *Bacillus subtilis* (Duncan, C. H., Wilson, G. A. and Young, F. E., Gene, 1, 153 (1977)). Alternatively, it is also possible to perform introduction into recipients for recombinant DNA after converting the DNA recipients into protoplasts or spheroplasts which easily incorporate recombinant DNA, as known for *Bacillus subtilis*, actinomycetes and yeasts (Chang, S. and Choen, S. N., *Molec. Gen. Genet.*, 168, 111 (1979); Bibb, M. J., Ward, J. M. and Hopwood, O. A., *Nature*, 274, 398 (1978); Hinnen, A., Hicks, J. B. and Fink, G. R., *Proc. Natl. Acad. Sci. USA*, 75, 1929 (1978)).

In the protoplast method, a sufficiently high frequency can be obtained even by the method used for *Bacillus subtilis* described above. It is of course possible to utilize a method in which DNA is incorporated into protoplasts of the genus Corynebacterium or Brevibacterium in the presence of polyethylene glycol or polyvinyl alcohol and divalent metal ion as described in Japanese Patent Laid-open No. 57-183799. An equivalent result is obtained even by a method in which incorporation of DNA is facilitated by addition of carboxymethyl cellulose, dextran, Ficoll, Pluronic F68 (Serva Co.) instead of polyethylene glycol or polyvinyl alcohol.

Further, recombinant DNA can be introduced into recipients belonging to bacteria of the genus Brevibacterium or Corynebacterium by using an electric pulse method (Sugimoto et al., Japanese Patent Laid-open No. 2-207791).

The wild type coryneform bacteria into which the mutant type HD gene or the deletion type HD gene is introduced are exemplified by bacteria belonging to the genus Corynebacterium, bacteria belonging to the genus Brevibacterium having been hitherto classified into the genus Brevibacterium but united as bacteria belonging to the genus Corynebacterium at present, and bacteria belonging to the genus Brevibacterium closely relative to bacteria belonging to the genus Corynebacterium. Especially, glutamate-producing bacteria belonging to the genus Corynebacterium (Brevibacterium) are most preferable in the present invention. Examples of wild strains of the glutamate-producing bacteria belonging to the genus Corynebacterium (Brevibacterium) includes the followings. These wild strains as well as strains added with a property of L-lysine production to such strains can be used for the present invention in the same manner.

| | |
|---|---|
| Corynebacterium acetoacidophilum | ATCC 13870 |
| Corynebacterium acetoglutamicum | ATCC 15806 |
| Corynebacterium callunae | ATCC 15991 |
| Corynebacterium glutamicum | ATCC 13032 |
| | ATCC 13060 |
| Brevibacterium divaricatum | ATCC 14020 |
| Brevibacterium lactofermentum | ATCC 13869 |
| Corynebacterium lilium | ATCC 15990 |
| Corynebacterium melassecola | ATCC 17965 |
| Brevibacterium saccharolyticum | ATCC 14066 |
| Brevibacterium immariophilum | ATCC 14068 |
| Brevibacterium roseum | ATCC 13825 |
| Brevibacterium flavum | ATCC 13826 |
| Brevibacterium thiogenitalis | ATCC 19240 |
| Microbacterium ammoniaphilum | ATCC 15354 |

The coryneform bacteria which can be used for the present invention includes mutant strains having glutamate productivity or those lacking glutamate productivity, in addition to the wild strains having glutamate productivity as described above. At present, various artificial mutant strains of coryneform glutamate-producing bacteria are used as L-lysine-producing bacteria, and these strains can be also used for the present invention. Such artificial mutant strains include the followings: AEC (S-(2-aminoethyl)-cysteine) resistant mutant strains; mutant strains which require amino acid such as L-homoserine (Japanese Patent Publication Nos. 48-28078 and 56-6499); mutant strains which exhibit resistance to AEC and require amino acids such as L-leucine, L-homoserine, L-proline, L-serine, L-arginine, L-alanine, and L-valine (U.S. Pat. Nos. 3708395 and 3825472); L-lysine-producing mutant strains which exhibit resistance to DL-α-amino-ε-caprolactam, α-amino-lauryllactam, aspartate-analog, sulfa drug, quinoid, N-lauroylleucine; L-lysine-producing mutant strains which exhibit resistance to inhibitors of oxyaloacetate decarboxylase or respiratory system enzymes (Japanese Patent Laid-open Nos. 50-53588, 50-31093, 52-102498, 53-9394, 53-86089, 55-9783, 55-9759, 56-32995 and 56-39778, and Japanese Patent Publication Nos. 53-43591 and 53-1833); L-lysine-producing mutant strains which require inositol or acetic acid (Japanese Patent Laid-open Nos. 55-9784 and 56-8692); L-lysine-producing mutant strains which exhibit sensitivity to fluoropyruvic acid or temperature not less than 34° C. (Japanese Patent Laid-open Nos. 55-9783 and 53-86090); and mutant strains of Brevibacterium or Corynebacterium which exhibit resistance to ethylene glycol and produce L-lysine (see U.S. patent application Ser. No. 333455).

<4> Amplification of AK gene in HD mutant strain or HD deficient strain

AK undergoes feedback inhibition in the case of co-existence of L-lysine and L-threonine. However, coryneform bacteria which do not express wild type homoserine dehydrogenase cannot produce L-threonine, and thus AK does not undergo feedback inhibition. Therefore, it is expected that the L-lysine productivity is improved if the AK gene is amplified in cells of coryneform bacteria which do not express wild type homoserine dehydrogenase. It is further expected that the L-lysine productivity is more improved if an inhibition-desensitized type AK gene is used as the AK gene to be amplified because feedback inhibition is more reduced.

The coryneform bacteria for introduction of the AK gene which do not express homoserine dehydrogenase are exemplified by the HD mutant strain or the HD deficient strain obtained as described in <3> above. However, the effect of improvement in L-lysine productivity is obtained owing to the amplification of the AK gene in the same manner even when an HD completely deficient strain obtained by a mutation treatment is used.

In order to amplify the AK gene or the mutant type AK gene in cells of such coryneform bacteria which do not express wild type homoserine dehydrogenase, the coryneform bacteria may be transformed with recombinant DNA comprising the AK gene or the mutant type AK gene and a vector autonomously replicable in cells of coryneform bacteria.

The vector used herein may be any one provided that it is autonomously replicable in cells of coryneform bacteria. Specifically, there may be exemplified pAJ655, pAJ1844, pAJ611, pAJ3148 and pAJ440 described above.

The method for transforming coryneform bacteria is exemplified by a method in which recipient cells are treated with calcium chloride to increase permeability of DNA as reported for *E. coli* K-12 (Mandel, M. and Higa, A., *J. Mol. Biol.*, 53, 159 (1970)), or a method in which introduction is performed in a growth stage so that cells can incorporate DNA (so-called competent cells) as reported for *Bacillus subtilis* (Duncan, C. H., Wilson, G. A. and Young, F. E., *Gene*, 1, 153 (1977)). Alternatively, it is also possible to perform introduction into recipients for recombinant DNA after converting the DNA recipients into protoplasts or spheroplasts which easily incorporate recombinant DNA, as known for *Bacillus subtilis*, actinomycetes and yeasts (Chang, S. and Choen, S. N., *Molec. Gen. Genet.*, 168, 111 (1979); Bibb, M. J., Ward, J. M. and Hopwood, O. A., *Nature*, 274, 398 (1978); Hinnen, A., Hicks, J. B. and Fink, G. R., *Proc. Natl. Acad. Sci. USA*, 75, 1929 (1978)).

Additionally, the stability of recombinant DNA in a host can be improved by allowing the vector to harbor a marker gene such as drug resistance, or a gene to supplement auxotrophy of the host.

A promoter inherent to the AK gene may be used exactly as it is for expressing the AK gene or the mutant type AK gene. However, it is also available that a promoter of another gene which operates in coryneform bacteria is used to ligate it with a DNA sequence coding for AK or mutant type AK.

<5> Introduction of mutant type AK gene into chromosomal DNA of HD mutant strain or HD deficient strain The L-lysine productivity can be improved by performing amplification of the AK gene in cells of the HD mutant strain or the HD deficient strain as described in <4> above. However, in order to increase the stability of the AK gene introduced into the HD mutant strain or the HD deficient strain, it is preferable to integrate the AK gene into chromosomal DNA. It is preferable herein to use a mutant type AK gene as the AK gene to be integrated into chromosomal DNA.

In order to integrate the mutant type AK gene into chromosomal DNA of a host, integration of the gene may be performed in the same manner as the mutant type HD gene or the deletion type HD gene. Namely, a temperature-sensitive replication origin originating from *Brevibacterium lactofermentum*, the mutant type AK gene, and a marker gene for providing resistance to a drug such as chloramphenicol are inserted into a plasmid vector to prepare recombinant DNA. The recombinant DNA is used to transform a coryneform bacterium, transformed strains are cultivated at a temperature at which the temperature-sensitive replication origin does not operate, and then they are cultivated in a medium containing the drug. Thus a transformed strain, in which the recombinant DNA is integrated into chromosomal DNA, is obtained.

The strain with the recombinant DNA integrated into the chromosomal DNA causes recombination with an AK gene sequence originally existing on the chromosome, in which two fused genes of the chromosomal AK gene and the mutant type AK gene are inserted into the chromosome in a state of interposing other portions of the recombinant DNA (vector portion, temperature-sensitive replication origin, and drug resistance marker). The mutant type AK is dominant in this state, and thus the phenotype is the mutant type. Therefore, the strain integrated with the gene may be used as it is. However, when approximately the same sequences are aligned in parallel on the chromosomal DNA, recombination may takes place again, and one of the AK genes is apt to fall off. Accordingly, it is preferable to obtain a gene-replaced strain in which only the mutant type AK gene remains on the chromosomal DNA. Namely, one copy of the AK gene is allowed to fall off together with the vector portion (including the temperature-sensitive replication origin and the drug resistance marker) by recombination of the two AK genes. For example, the strain with the integration on the chromosome is cultivated, and cultivated bacterial cells are spread and cultivated on a solid plate medium containing no drug. Grown colonies are replicated and cultivated on a solid plate medium containing the drug, and drug-sensitive strains are obtained. The fact that the vector portion falls off from chromosomes of the obtained drug-sensitive strains is confirmed by Southern hybridization, and the fact that the mutant type AK is expressed is confirmed.

No problem arises even when the wild type AK gene remains on the chromosomal DNA in a complete form, as being different from the case of the gene replacement using the mutant type HD gene or the deletion type HD gene. Accordingly, the mutant type AK gene may be integrated at a site other than that for the AK gene on the chromosomal DNA.

<6> Production of L-lysine

L-lysine can be produced and accumulated in a culture by cultivating, in an appropriate medium, the HD mutant strain, the HD deficient strain, the strains of these types in which the AK gene is amplified, or the HD mutant strain or the HD deficient strain into which the mutant type AK gene is integrated.

The medium to be used includes an ordinary medium containing a carbon source, a nitrogen source, inorganic ions and optionally other organic components.

As the carbon source, it is possible to use sugars such as glucose, lactose, galactose, fructose, or starch hydrolysate; or organic acids such as fumaric acid, citric acid or succinic acid.

As the nitrogen source, it is possible to use inorganic ammonium salts such as ammonium sulfate, ammonium chloride or ammonium phosphate; organic nitrogen such as soybean hydrolysate; ammonia gas; or aqueous ammonia.

It is desirable to allow required substances such as vitamin $B_1$ and L-homoserine or yeast extract to be contained in appropriate amounts as organic trace nutrients. Other than the above, potassium phosphate, magnesium sulfate, iron ion, manganese ion and the like are added in small amounts, if necessary.

When the HD deficient strain is used, L-threonine and L-methionine, or L-homoserine is added to the medium in appropriate amount(s).

Cultivation is preferably carried out under an aerobic condition for 16–72 hours. The cultivation temperature is preferably controlled at 25° C. to 37° C., and pH is preferably controlled at 5–7 during cultivation. Inorganic or organic, acidic or alkaline substances as well as ammonia gas or the like can be used for pH adjustment. Collection of L-lysine from a cultivated liquor may be carried out by combining an ordinary ion exchange resin method, a precipitation method and other known methods.

BRIEF DESCRIPTION OF THE DRAWINGS

FIG. 2 is a view of comparison of amino acid sequences of HD genes of various microorganisms (SEQ ID NO: 20–22);

FIG. 3 is a view of comparison of amino acid sequences of HD genes of various microorganisms (continued);

DESCRIPTION OF PREFERRED EMBODIMENTS

Figure 1:
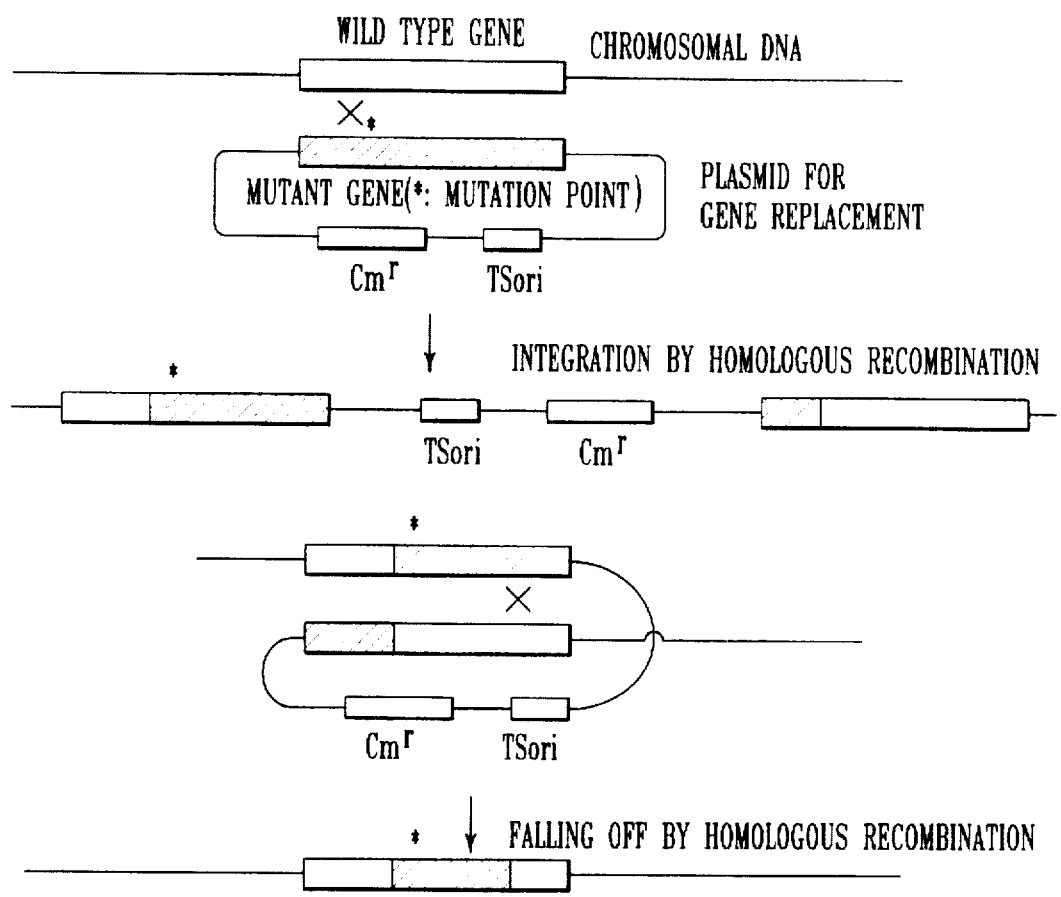
FIG. 1 is a conceptual view of gene integration and gene replacement.

The present invention will be more concretely explained below with reference to Examples.

EXAMPLE 1

Analysis of Wild Type HD Gene, Leaky Type HD Gene, and Inhibition-Desensitized Type HD Gene Leaky type HD mutant strains and a mutant strain for producing HD with desensitized feedback inhibition by L-threonine were created from a wild strain of *Brevibacterium lactofermentum*. A wild type HD gene, leaky type HD genes and a inhibition-desensitized type HD gene were isolated from the wild and mutant strains, and analysis of their structures was performed. *Brevibacterium lactofermentum* AJ12036 strain (FERM BP-734) was used as the wild strain. *Brevibacterium lactofermentum* AJ12472 and AJ12937 strains were used as the leaky type HD mutant strains. *Brevibacterium lactofermentum* AJ6080 strain was used as the inhibition-desensitized type HD mutant strain. These mutant strains were obtained as follows.

The AJ12036 strain is a strain obtained by deleting an originally existing plasmid, pAM330 from *Brevibacterium lactofermentum* 2256 strain (ATCC 13869), which produces wild type HD with respect to HD.

The AJ12472 and AJ12937 strains are strains obtained from *Brevibacterium lactofermentum* 2256 strain (ATCC 13869) as a result of repeated breeding by mutation using L-lysine productivity as an index, which produce leaky type HD's. The AI6080 stain is a stain obtained from *Brevibacterium lactofermentum* 2256 strain (ATCC 13869) as a result of repeated breeding by mutation using L-threonine productivity as an index, which produces inhibition-desensitized type HD.

<1> Amplification of HD gene by PCR method

A nucleotide sequence of the HD gene has been reported for *Corynebacterium glutamicum* (Peoples, O. P. et al, *Molecular Microbiology*, 2(1), 63–72 (1988)). It was speculated that the similarity of each HD gene sequence might be high between *Brevibacterium lactofermentum* and *Corynebacterium glutamicum*. Thus synthetic primer DNA's were prepared on the basis of the sequence of *Corynebacterium glutamicum* for use in the PCR method.

Chromosomal DNA's were prepared in accordance with an ordinary method from *Brevibacterium lactofermentum* AJ12036, AJ12472, AJ12937 and AI6080 strains. In order to amplify DNA fragments of about 1500 bp containing HD genes from these chromosomal DNA's, a DNA synthesizer Model 1381A (ABI Ltd.) was used to synthesize two species of primers of a 5' side primer H1 ((841)5'-CTGGG AAGGTGAATCGAATTT-3' (860), SEQ ID NO: 1 in Sequence Listing) and a 3' side primer H2 ((2410)5'-TCCGAGGTTTGCA GAAGATC-3' (2391), SEQ ID NO: 2 in Sequence Listing). Numbers in the parentheses indicate positions in the nucleotide sequence published by People et al. (Peoples, O. P. et al. *Molecular Microbiology*, 2(1), 63–72 (1988)). Obtained synthetic primers were purified by reversed phase HPLC.

The PCR was performed with a composition shown below using a PCR amplification apparatus (DNA Thermal Cycler PJ2000 produced by Takara Shuzo Co., Ltd.) and a PCR kit (Takara GeneAmp™ kit produced by Takara Shuzo Co., Ltd.).

TABLE 1

| Component | Concentration | Blended amount |
|---|---|---|
| Primer H1 | 0.25 µM | 25 pmol |
| Primer H2 | 0.25 µM | 25 pmol |
| dATP, dGTP, dTTP, dCTP | each 200 µM | 20 nmol |
| Taq DNA polymerase | 2.5 U/100 µL | 0.5 µL (5 U/µL) |
| Chromosomal DNA | | 1 µg |
| 10 × reaction buffer | | 10 µL |
| Water | | balance |
| | | (total amount: 100 µL) |

Conditions for denaturation of DNA, annealing of DNA, and polymerase reaction in the PCR were at 94° C. for 1 minute, at 37° C. for 2 minutes and at 75° C. for 3 minutes respectively, and transition between each of the temperatures was performed for 1 second. DNA was amplified by repeating the reaction cycle by 25 cycles. As a result of confirmation of sizes of amplification reaction products thus obtained by using agarose gel electrophoresis, amplification of DNA fragment of about 1.4 Kbp was observed.

Thus the DNA fragments amplified from the chromosomal DNA of each of the AJ12036, AJ12472, AJ12937 and AI6080 strains were respectively cut with a restriction enzyme KpnI to obtain DNA fragments which were inserted into a KpnI site of a vector plasmid pHSG399 (see Takeshita, S. et al., *Gene* (1987), 61, 63–74) to obtain recombinant DNA's. The recombinant DNA's containing amplified fragments originating from the AJ12036, AJ12472, AJ12937 and AI6080 strains were designated as PHDW, pHDMI, pHDMII and pHDMIII, respectively. Each of the plasmids was introduced into *E. coli* JM109 strain to obtain transformants.

<2> Determination of nucleotide sequences of HD genes and analysis of mutation points (1) Comparison of nucleotide sequences of wild and mutant type HD genes Nucleotide sequences of the HD gene fragments of *Brevibacterium lactofermentum* AJ12036, AJ12472, AJ12937 and AI6080 strains obtained as described above were determined by the dideoxy method.

A determined nucleotide sequence of the wild type HD gene of the AJ12036 strain, and an amino acid sequence deduced from the sequence are shown in SEQ ID NO: 3 in Sequence Listing. Further, the amino acid sequence is shown in SEQ ID NO: 4 in Sequence Listing. As a result of comparison of the sequence with the sequence of the HD gene of *Corynebacterium glutamicum* reported by Peoples et al. (Peoples, O. P. et al. *Molecular Microbiology*, 2(1), 63–72 (1988)), nucleotides were different at 4 places, and one of them was different at the amino acid level. The different points are shown below using the sequence of the HD gene of *Corynebacterium glutamicum* as a standard.

(1) $^{531}G \rightarrow C$ ($^{148}Gly \rightarrow ^{148}Ala$)

(2) $^{1222}G \rightarrow C$ (3) $^{1318}G \rightarrow T$ (4) $^{1324}C \rightarrow G$ Such a diversity observed among HD genes of wild type strains of coryneform bacteria do not affect the HD activity, and the sequence of the HD gene of *Corynebacterium glutamicum* may be treated as equivalent of the sequence of the HD gene of *Brevibacterium lactofermentum* shown in SEQ ID NO: 3.

As a result of comparison of the nucleotide sequence of the wild type HD gene and the amino acid sequence deduced from the sequence of the AJ12036 strain with nucleotide sequences of the HD genes and amino acid sequences of the AJ12472, AJ12937 and AI6080 strains, mutation points were found for the AJ12472 strain at 2 places, for AJ12937 at 1 place, and for AI6080 at 1 place, all accompanying amino acid replacement. Further, it was found that exactly the same mutation was commonly present in the HD genes of the AJ12472 and AJ12937 strains at 1 place. Each of the mutation points is shown below.

TABLE 2

| Bacterial strain | Difference in nucleotide sequence | Mutation in amino acid residue |
|---|---|---|
| AJ12472 strain | $^{155}G \rightarrow T$ | $^{23}Leu \rightarrow Phe$ |
|  | $^{398}G \rightarrow A$ | $^{104}Val \rightarrow Ile$ |
| AJ12937 strain | $^{398}G \rightarrow A$ | $^{104}Val \rightarrow Ile$ |
| AI6080 strain | $^{1266}C \rightarrow T$ | $^{393}Ser \rightarrow Phe$ |

Hereinafter, the mutation point of $^{155}G \rightarrow T$ ($^{23}Leu \rightarrow Phe$) is referred to as "mutation point 1", the mutation point of $^{398}G \rightarrow A$ ($^{104}Val \rightarrow Ile$) is referred to as "mutation point 2", and the mutation point of $^{1266}C \rightarrow T$ ($^{393}Ser \rightarrow Phe$) is referred to as "mutation point 3".

(2) Comparison of HD amino acid sequences and mutation points of *Brevibacterium lactofermentum*, *Bacillus subtilis* and *E. coli*

It is known that two kinds of HD genes (HD-1, HD-2) are present in *E. coli*, and any of them constitutes bifunctional enzyme with AK (Zakin, M. M. et al., *J. B. C.*, 258, 3028–3031 (1983)). Further, a nucleotide sequence of an HD gene of *Bacillus subtilis* has been also determined (Parsot, C. and Cohen, G. N., *J. B. C.*, 263(29), 14654–14660 (1988)). Comparison of these amino acid sequences with the amino acid sequence of the wild type HD of *Brevibacterium lactofermentum* is shown in FIGS. 2 and 3.

According to the result, it is understood that most of sites having high homology are located in a region on the N-terminal side, and that sites having high homology are concentrated in a region having amino acid numbers of 100–230 especially in the amino acid sequence of HD of *Brevibacterium lactofermentum*. It is postulated that the active region of HD exists on the N-terminal side according to the aforementioned fact, the fact that the two mutation points of HD of *Brevibacterium lactofermentum* are located within about 100 amino acid residues from the N-terminal, especially the mutation point 1 is located at a position of 23 amino acid residues from the N-terminal, and the two mutation points are amino acid residues having high conservation with respect to HD-1 and HD-2 of *E. coli*, HD of *Bacillus subtilis*, and HD of *Brevibacterium lactofermentum*, and the fact that no sequence corresponding to about 100 amino acid residues on the C-terminal side of HD of *Brevibacterium lactofermentum* is present in HD-1 and HD-2 of *E. coli*.

On the other hand, nucleotide sequences of HD genes of *Corynebacterium glutamicum* with desensitized inhibition by L-threonine have been published. Namely, Sahm et al. have reported replacement of one 68th amino acid from the C-terminal due to point mutation (Reinscheid, D. J. et al., *J. Bacteriol.*, 173(10), 3228–3230 (1991)), and Sinskey et al. have reported change in 17th amino acid and followings due to frame shift on account of point mutation, and deletion of 7th amino acid and followings from the C-terminal (Archer, J. A. C. et al., *Gene*, 107, 53–59 (1991)). Further, the mutation of amino acid residue was at a position of 53th amino acid residue from the C-terminal in the inhibition-desensitized HD of the *Brevibacterium lactofermentum* AI6080 strain. Furthermore, the region on the C-terminal side which does not exist in HD-1 and HD-2 of *E. coli* exists in HD of *Bacillus subtilis* which undergoes feedback inhibition by L-threonine in the same manner as HD of *Brevibacterium lactofermentum*. Accordingly, it is speculated that the region of HD relating to the feedback inhibition by L-threonine exists on the C-terminal side.

EXAMPLE 2

Preparation and Analysis of Wild Type AK Gene and Mutant Type AK Gene

<1> Construction of wild type and mutant type AK genes and plasmids containing them Chromosomal DNA's were prepared in accordance with an ordinary method from *Brevibacterium lactofermentum* 2256 strain (ATCC 13869) and an L-lysine-producing mutant strain AJ3463 (FERM P-1987) obtained from the 2256 strain by a mutation treatment. AK genes were amplified from the chromosomal DNA's in accordance with the PCR method (polymerase chain reaction; see White, T. J. et al., *Trends Genet.*, 5, 185 (1989)). DNA primers used in the amplification were based on a sequence known for *Corynebacterium glutamicum* (see *Molecular Microbiology* (1991), 5(5), 1197–1204, and *Mol. Gen. Genet.* (1990), 224, 317–324). In order to amplify a region of about 1643 bp coding for the AK gene, single strand DNA's of 23 mer and 21 mer having sequences of 5'-TCGCGAAGTAGCACCTGTCACTT-3' (SEQ ID NO: 5) and 5'-ACGGAATTCAATCTTACGGCC-3' (SEQ ID NO: 6) were synthesized. The DNA's were synthesized by using a DNA synthesizer Model 380B produced by Applied Biosystems, Ltd. in accordance with an ordinary method using the phosphoamidito method (see *Tetrahedron Letters* (1981), 22, 1859).

In the PCR, gene amplification was performed by using DNA Thermal Cycler Model PJ2000 produced by Takara Shuzo Co., Ltd., using Taq DNA polymerase in accordance with a method designated by the supplier. After confirming an amplified gene fragment of 1643 kb by agarose gel electrophoresis, the fragment excised from the gel was purified in accordance with an ordinary method, and cut with restriction enzymes NruI (produced by Takara Shuzo Co., Ltd.) and EcoRI (produced by Takara Shuzo Co., Ltd.).

pHSG399 (see Takeshita, S. et al., *Gene* (1987), 61, 63–74) was used for a vector for cloning the gene fragment. pHSG399 was cut with a restriction enzyme SmaI (produced by Takara Shuzo Co., Ltd.) and a restriction enzyme EcoRI, and ligated with the amplified AK gene fragment. The ligation of DNA was performed in accordance with a designated method by using a DNA ligation kit (produced by Takara Shuzo Co., Ltd.). Thus a plasmid was prepared in which pHSG399 is connected to the AK gene product amplified from the chromosome of Brevibacterium. A plasmid having the AK gene originating from the 2256 strain (ATCC 13869) as a wild strain was designated as p399AKY, and a plasmid having the AK gene originating from AJ3463 as an L-lysine-producing bacterium was designated as p399AK9.

A DNA fragment having an ability to enable plasmids to make autonomous replication in bacteria belonging to the genus Corynebacterium (hereinafter referred to as "Coryne.-ori") was introduced into p399AKY and p399AK9 respectively, to prepare plasmids carrying the AK genes autonomously replicable in bacteria belonging to the genus Corynebacterium. Coryne.-ori was prepared from a plasmid vector autonomously replicable in bacterial cells of both *Escherichia coli* and bacteria belonging to the genus Corynebacterium. Some of such plasmid vectors have been reported. However, in this case, a shuttle vector pHK4 was used which was prepared from a plasmid pAJ1844 autonomously replicable in cells of coryneform bacteria (see Japanese Patent Laid-open No. 58-216199) and a plasmid pHSG298 autonomously replicable in cells of *Escherichia coli* (see Takeshita, S. et al., *Gene*, 61, 63–74 (1987)).

The preparation method for pHK4 is described in detail in Japanese Patent Laid-open No. 5-7491, however, it may be outlined as follows. pAJ1844 was partially cut with a restriction enzyme Sau3AI, and ligated with pHSG298 completely cut with a restriction enzyme BamHI. DNA after the ligation was introduced into *Brevibacterium lactofermentum* AJ12036 (FERM-P7559). An electric pulse method (see Japanese Patent Laid-open No. 2-207791) was used as a method for transformation. Selection of transformants was performed by using M-CM2G plates containing 25 μg/ml of kanamycin (containing 5 g of glucose, 10 g of polypeptone, 10 g of yeast extract, 5 g of NaCl, 0.2 g of DL-methionine and 15 g of agar in 1 l of pure water (pH 7.2)). Plasmids were prepared from transformants, and one having the smallest size was selected and designated as pHK4. This plasmid can make autonomous replication in *Escherichia coli* and coryneform bacteria, and gives kanamycin resistance to a host.

pHK4 obtained as described above was cut with a restriction enzyme KpnI (produced by Takara Shuzo Co., Ltd.), and cut faces were blunt-ended. Formation of blunt ends was performed in accordance with a designated method by using a DNA Blunting kit (produced by Takara Shuzo Co., Ltd.).

After the blunt end formation, a phosphatized BamHI linker (produced by Takara Shuzo Co., Ltd.) was connected, to make modification to allow a DNA fragment of the Coryne.-ori portion to be cut from pHK4 with only BamHI. This plasmid was cut with BamHI. A generated Coryne.-ori DNA fragment was ligated with p399AKY or p399AK9 having been cut with BamHI in the same manner, to prepare a plasmid autonomously replicable in bacteria belonging to the genus Corynebacterium and contained the AK gene.

Figure 4:
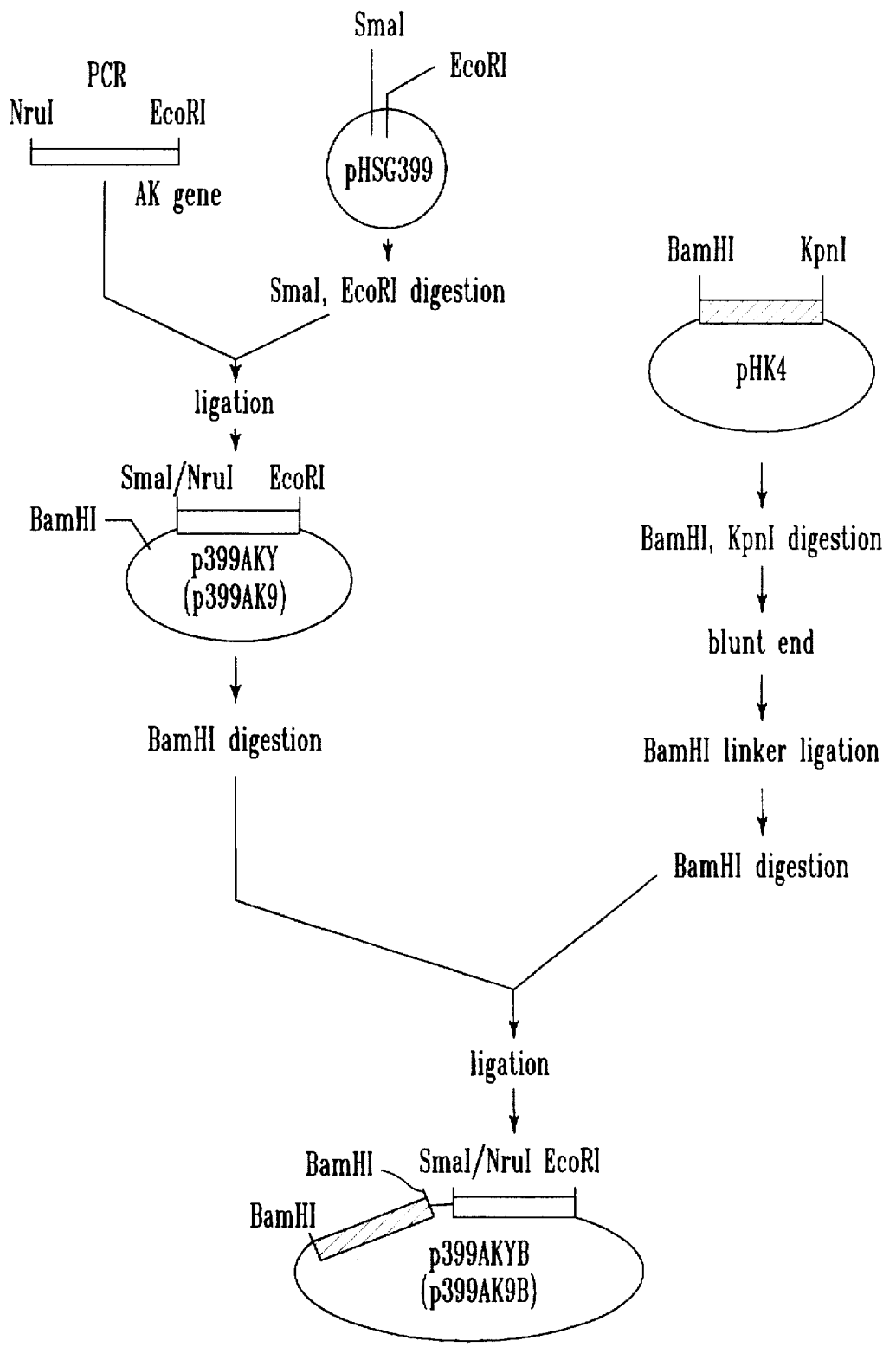
FIG. 4 shows process of construction of p399AK9B and p399AKYB.

A plasmid containing the wild type AK gene originating from p399AKY was designated as p399AKYB, and a plasmid containing the mutant type AK gene originating from p399AK9 was designated as p399AK9B. Process of construction of p399AK9B and p399AKYB is shown in FIG. 4. A strain AJ12691 obtained by introducing the mutant type AK plasmid p399AK9B into the AJ12036 strain (FERM-P7559) as a wild type strain of Brevibacterium lactofermentum has been deposited on Apr. 10, 1992 in National Institute of Bioscience and Human Technology of Agency of Industrial Science and Technology under a deposition number of FERM P-12918, transferred to international deposition based on the Budapest Treaty on Feb. 10, 1995, and deposited under a deposition number of FERM BP-4999.

<2> Determination of nucleotide sequences of wild type and mutant type AK genes of Brevibacterium lactofermentum The plasmid p399AKY containing the wild type AK gene and the plasmid p399AK9 containing the mutant type AK gene were prepared from each of the transformants, and nucleotide sequences of the wild and mutant type AK genes were determined. The determination of the nucleotide sequences was performed in accordance with a method of Sanger (F. Sanger et al., Proc. Natl. Acad. Sci., 74, 5463 (1977) and so on).

The nucleotide sequence of the wild type AK gene encoded by p399AKY is shown in SEQ ID NO: 7 in Sequence Listing. On the other hand, the nucleotide sequence of the mutant type AK gene encoded by p399AK9 only had mutation of one base pair in which 1051th G was changed to A in SEQ ID NO: 7 as compared with the wild type AK. It is known for the AK gene that two subunits of α, β are encoded on an identical DNA strand in an identical reading frame (see Kalinowski, J. et al., Molecular Microbiology (1991), 5(5), 1197-1204). Judging from homology, it is speculated for the gene of this case that two subunits of α, β are encoded on an identical DNA strand in an identical reading frame.

An amino acid sequence of the α-subunit of the wild type AK protein deduced from the nucleotide sequence of DNA is shown in SEQ ID NO: 8 in Sequence Listing simultaneously with the DNA sequence. Only the amino acid sequence is shown in SEQ ID NO: 9. An amino acid sequence of the β-subunit of the wild type AK protein deduced from the nucleotide sequence of DNA is shown in SEQ ID NO: 10 in Sequence Listing simultaneously with the DNA sequence. Only the amino acid sequence is shown in SEQ ID NO: 11. Each of the subunits uses GTG as a start codon, and a corresponding amino acid is represented as methionine. However, this represents methionine, valine or formylmethionine.

On the other hand, the mutation on the mutant type AK gene sequence indicates occurrence of replacement of amino acid residues such that a 279th alanine residue is replaced with a threonine residue in the α-subunit, and a 30th alanine residue is replaced with a threonine residue in the β-subunit, with respect to the amino acid sequences (SEQ ID NOS: 8 and 10) of the wild type AK protein.

<3> AK activity of expression product of mutant type AK gene and evaluation of desensitization of inhibition Strains were prepared in which the wild type AK plasmid p399AKYB and the mutant type AK plasmid p399AK9B were respectively introduced into the AJ12036 strain (FERM-P7559) as a wild type strain of Brevibacterium lactofermentum (Corynebacterium glutamicum). The gene introduction into Corynebacterium was performed in accordance with an electric pulse method. The AK activity was measured for Brevibacterium lactofermentum (Corynebacterium glutamicum) AJ12036 strain as the host, an AJ12690 strain harboring the wild type AK plasmid, and an AJ12691 (FERM-P12918) strain harboring the mutant type AK plasmid. The measurement of the activity was performed in accordance with an ordinary method (see Miyajima, R. et al., The Journal of Biochemistry (1968), 63(2), 139-148).

As shown in Table 3, it has been confirmed that owing to the introduction of the AK plasmids, the specific activity of AK is increased about 10-15 times, and that the cumulative inhibition by L-lysine and L-threonine is desensitized only for the strain with the introduced mutant type AK plasmid. Table 3 shows the AK specific activity and the degree of its cumulative inhibition by L-lysine and L-threonine with respect to solutions obtained by destroying bacterial cells of the wild type AJ12036 strain of Brevibacterium lactofermentum, the AJ12690 strain allowed to harbor the wild type AK plasmid, and the AJ12691 strain allowed to harbor the mutant type AK plasmid. L-lysine and L-threonine as inhibitors were added to give a final concentration of 1 mM, respectively.

TABLE 3

| | AK specific activity (mU/mg protein) | |
|---|---|---|
| Bacterial strain | No addition | +1 mM L-lysine, +1 mM L-threonine |
| AJ12036 | 19.0 | 2.6 |
| AJ12690 | 235.3 | 34.6 |
| AJ12691 | 210.5 | 145.3 |

<4> Improvement of mutant type AK gene by site-specific mutation

In order to further improve the mutant type AK obtained as described above, it was intended to replace the mutation point ($^{279}$Ala→Thr) of the mutant type AK with another amino acid residue by means of site-specific mutation. The method for site-specific mutation for causing desired mutation at a desired site includes, for example, a method using PCR (Higuchi, R., 61, in PCR Technology (Erlich, H. A. Eds., Stockton Press (1989))), a method using phage (Kramer, W. and Frits, H. J., Meth. in Enzymol., 154, 350 (1987); Kunkel, T. A. et al., Meth. in Enzymol., 154, 367 (1987)).

With respect to the species of amino acid residues to be introduced by mutation, 20 species of amino acids were classified in accordance with respective properties such as polarity and molecular structure, and representative 8 species (Arg, Asp, Cys, Phe, Pro, Ser, Tyr, Val) were selected. Amino acid mutation and nucleotide replacement at respective mutation points are shown in Table 4.

TABLE 4

| Identification of mutation | Mutation point and amino acid change |
|---|---|
| Thr | $^{279}$Ala GCT → Thr A*CT |
| Arg | $^{279}$Ala GCT → Arg C*G*T |
| Asp | $^{279}$Ala GCT → Asp GA*T |
| Cys | $^{279}$Ala GCT → Cys T*G*T |
| Phe | $^{279}$Ala GCT → Phe T*T*T |
| Pro | $^{279}$Ala GCT → Pro C*CT |
| Ser | $^{279}$Ala GCT → Ser T*CT |
| Tyr | $^{279}$Ala GCT → Tyr T*A*T |
| Val | $^{279}$Ala GCT → Val GT*T |

A method for introducing mutation used herein is as follows. Eight species of synthetic DNA of 23 mers, in which the codon for the 279th Ala residue for introducing mutation was replaced with codons for desired amino acid residues, were designed (5'-GCCAGGCGAG CGT GCCAAGGTTT-3': SEQ ID NO: 12 as synthetic DNA for introducing Arg; 5'-GCCAGGCGAG GAT GCCAAGGTTT-3': SEQ ID NO: 13 as synthetic DNA for introducing Asp; 5'-GCCAGGCGAG TGT GCCAAGGTTT-3': SEQ ID NO: 14 as synthetic DNA for introducing Cys; 5'-GCCAGGCGAG TTT GCCAAGGTTT-3': SEQ ID NO: 15 as synthetic DNA for introducing Phe; 5'-GCCAGGCGAG CCT GCCAAGGTTT-3': SEQ ID NO: 16 as synthetic DNA for introducing Pro; 5'-GCCAGGCGAG TCT GCCAAGGTTT-3': SEQ ID NO: 17 as synthetic DNA for introducing Ser; 5'-GCCAGGCGAG TAT GCCAAGGTTT-3': SEQ ID NO: 18 as synthetic DNA for introducing Tyr; and 5'-GCCAGGCGAG GTT GCCAAGGTTT-3': SEQ ID NO: 19 as synthetic DNA for introducing Val). Sixteen species of 23 mer single strand DNA's were synthesized together with their complementary sequences.

When an Arg residue is introduced, for example, the single strand DNA having the sequence 5'-GCCAGGCGAG CGT GCCAAGGTTT-3' (SEQ ID NO: 12), the single strand DNA as its complementary chain, the single strand DNA having the sequence of SEQ ID NO: 5, and the single strand DNA having the sequence of SEQ ID NO: 6 were used as primers, and the PCR method was performed using p399AKY as a template. In order to avoid introduction of nonspecific mutation, about 280 base pairs containing the mutation point were excised from prepared DNA with restriction enzymes (NaeI-AvaII), and replaced with a corresponding site of p399AKY to prepare a recombinant plasmid. The nucleotide sequence was confirmed for the replaced region.

Upon measurement and evaluation of the enzyme activities of the mutant type AK's harbored by each of 8 species of obtained recombinant plasmids, an AK completely deficient strain of E. coli, Gif106M1 was used as a host (Boy, E. and Patte, J. C., J. Bacteriol., 112, 84–92 (1972); Theze, J. et al., J. Bacteriol., 117, 133–143 (1974)), because no AK deficient strain was known for coryneform bacteria. Otherwise, AK of a host and AK from the plasmid may exist in a mixed manner, probably resulting in inaccurate measurement. Many genes of coryneform bacteria are known to be expressed in E. coli. Thus it was postulated that the AK gene could be expressed in Escherichia coli since it was linked downstream from a lac promoter on pHSG399.

E. coli Gif106M1 was transformed with the recombinant plasmids of the wild type and the eight species, cell-free extracts were prepared from each of transformed strains, and analysis of enzyme was performed. The AK activity was measured in accordance with a method described in Miyajima, R. et al., The Journal of Biochemistry (1968), 63(2), 139–148. The degree of inhibition desensitization and the specific activity are shown in Table 5, in the case of addition of 5 mM of L-lysine, 5 mM of L-threonine, or each 2 mM of L-lysine and L-threonine.

TABLE 5

| | Specific activity (mU/mg protein) | 5 mM Lys (%) | 2 mM Thr (%) | 2 mM Lys + Thr (%) |
|---|---|---|---|---|
| AJ12036 | 5.6 | 52.0 | 87.0 | 7.0 |
| Wild type | 316.4 | 52.7 | 86.8 | 6.2 |
| Thr | 374.4 | 58.7 | 109.1 | 78.3 |
| Arg | 197.4 | 41.4 | 106.8 | 58.6 |
| Cys | 267.0 | 66.5 | 135.7 | 60.6 |
| Phe | 447.7 | 14.6 | 105.0 | 32.4 |
| Pro | 125.0 | 77.5 | 123.2 | 85.2 |
| Ser | 406.8 | 55.0 | 114.4 | 37.0 |
| Tyr | 425.6 | 16.1 | 104.8 | 32.2 |
| Val | 448.9 | 60.5 | 103.5 | 75.5 |

As a result, AK was inactivated in the case of change to acidic amino acid such as Asp, while the inhibition by L-lysine and L-threonine was desensitized in the case of change to any other amino acid.

EXAMPLE 3

Evaluation of L-lysine Productivity of HD Mutant Strain and HD Deficient Strain In order to compare effects on the L-lysine productivity exerted by the two kinds of mutant type HD and the HD deficiency, mutant type HD genes or an HD gene with a part of its sequence deleted was integrated into chromosome of an identical host to prepare gene-replaced strains each of which was used as HD mutant strains and an HD deficient strain, and evaluated for the L-lysine productivity.

<1> Preparation of plasmids for replacing mutant type HD genes and plasmid for replacing deficient type HD gene Plasmids for gene replacement were prepared for introduction by homologous recombination of mutant type HD genes or an HD gene with a part of its sequence deleted, into chromosomal DNA of Brevibacterium lactofermentum AJ12036 strain (FERM BP-734) (obtained by deleting a cryptic plasmid, pAM330 from Brevibacterium lactofermentum 2256 strain (ATCC 13869)).

(1) Preparation of HD gene having mutation point 1

The mutant type HD genes obtained in Example 1 were two species including the mutant type HD gene (from AJ12472 strain) having the mutation point 1 ($^{155}$C→T ($^{23}$Leu→Phe)) and the mutation point 2 ($^{398}$G→A ($^{104}$Val→Ile)), and the mutant type gene (from AJ12937) having only the mutation point 2. In order to investigate the influence exerted by the mutation point 1 on the HD activity and the L-lysine productivity, a mutant type HD gene having only the mutation point 1 was prepared. Hereinafter, the mutant type HD having the mutation point 1 is referred to as HD-M1, the mutant type HD having the mutation point 2 is referred to as HD-M2, and the mutant type HD having both the mutation points 1 and 2 is referred to as HDM-12.

The plasmid pHDMI containing the HDM-12 gene was cut with a restriction enzyme TthIII1 for cutting between the both mutation points of 1 and 2, and KpnI for cutting a ligation point between the vector and the HD gene, to obtain a 5' side HD fragment having the mutation point 1. In the same manner, pHDW having the wild type HD gene was cut with TthIII1 and KpnI to obtain a 3' side HD fragment. The HD-M1 gene having only the mutation point 1 was obtained by ligating the 5' side HD fragment with the 3' side HD fragment thus obtained.

(2) Construction of plasmids for gene replacement

The HD-M1 gene having only the mutation point 1 obtained as described above was inserted into a KpnI site of a vector plasmid pHSG398 having a chloramphenicol resistance (Cm$^r$) gene. Further, a temperature-sensitive replication origin (TSori) originating from *Brevibacterium lactofermentum* wild strain was introduced into a BamHI site of pHSG398. Thus a plasmid pTSHDM1 for replacing the HD-M1 gene was constructed. TSori was prepared from a plasmid pHSC4 (see Japanese Patent Laid-open No. 5-7491) obtained by treating a plasmid pHK4 having Coryne.-ori with hydroxylamine in vitro, transforming *Brevibacterium lactofermentum* AJ12036 with plasmid DNA after the treatment, and recovering the plasmid from a transformed strain incapable of growth at a high temperature (34° C.). Coryne.-ori can be excised from pHSC4 with BamHI and KpnI, however, the plasmid was modified to allow Coryne.-ori to be excised only by cutting with BamHI. pHSC4 was cut with a restriction enzyme KpnI (produced by Takara Shuzo Co., Ltd.), and cut faces were blunt-ended. Formation of blunt ends was performed in accordance with a designated method using a DNA Blunting kit (produced by Takara Shuzo Co., Ltd.). After the blunt end formation, a phosphatized BamHI linker (produced by Takara Shuzo Co., Ltd.) was connected, to make modification to allow a DNA fragment of the TSori portion to be excised from pHSC4 with only BamHI. *Escherichia coli* AJ12571 harboring pHSC4 has been deposited on Oct. 11, 1990 in National Institute of Bioscience and Human Technology of Agency of Industrial Science and Technology under a deposition number of FERM P-11763, transferred to international deposition based on the Budapest Treaty on Aug. 26, 1991, and deposited under a deposition number of FERM BP-3524.

Next, in the same manner, the plasmid pHDII having the HD-M2 gene having only the mutation point 2 was cut with KpnI to obtain an HD-M2 gene fragment which was inserted into a KpnI site of pHSG398. Subsequently, TSori was inserted into a BamHI site. Thus a plasmid pTSHDM2 for replacing the HD-M2 gene was constructed.

Further, the plasmid pHDMI having the HD-M12 gene having both the mutation points 1 and 2 was cut with KpnI to obtain an HD-M12 gene fragment which was inserted into a KpnI site of pHSG398. Subsequently, TSori was inserted into a BamHI site. Thus a plasmid pTSHDM12 for replacing the HD-M12 gene was constructed.

Further, the plasmid pHDW having the wild type HD gene was cut with AatII, and a portion between two AatII sites (nucleotide numbers of 716–722 and 1082–1087 in SEQ ID NO: 3) existing in the HD gene was deleted. Thus a plasmid containing an HD gene with its part deleted (HD-Δ gene) was prepared. This plasmid was cut with KpnI to obtain an HD-Δ gene fragment which was inserted into a KpnI site of pHSG398. Subsequently TSori was inserted into a BamHI site. Thus a plasmid pTSHDΔ for replacing the HD-Δ gene was constructed.

(3) Preparation of HD mutant strain and HD deficient strain

Transformation of *Brevibacterium lactofermentum* AJ12036 strain was performed in accordance with an electric pulse method (Sugimoto et al., Japanese Patent Laid-open No. 2-207791) by using the plasmids for replacing the mutant type HD genes pTSHDM1, pTSHDM2 and pTSHDM12, and the plasmid for replacing the deletion type HD gene pTSHDΔ obtained as described above.

Obtained transformed strains were cultivated by using an M-CM2G medium at 25° C. until full growth (about 1–2×10$^9$/ml) was achieved. Cultivated bacterial cells were diluted to give 10$^5$ cells per one plate, spread on an M-CM2G solid plate medium containing chloramphenicol (5 μg/mL), and cultivated at 34° C. for 2–7 days to obtain colonies. It was confirmed for the obtained colonies that no plasmid was contained in cells. Further, it was confirmed that the plasmids for gene replacement were integrated into chromosome by means of Southern hybridization analysis using linear pHSG398 as a probe.

In the strain of chromosomal integration obtained as described above, two fused genes of an HD gene originally existing on the chromosome and the mutant type or deletion type HD gene are inserted in a state of interposing the vector (including TSori).

Next, in order to leave only the mutant type HD gene or the deletion type HD gene on the chromosome, the wild type HD gene and the vector were allowed to fall off from the chromosomal DNA to obtain strains replaced with the mutant type HD genes and a strain replaced with the deletion type HD gene. The wild type HD gene and the vector were allowed to fall off as follows.

Each of the integrated strains was cultivated at 34° C. in an M-CM2G medium containing chloramphenicol (10 μg/mL) until full growth (1–2×10$^9$) was achieved. Cultivated bacterial cells were spread on an M-CM2G solid plate medium containing no chloramphenicol to give 50–200 colonies per one plate, and cultivated at 34° C. Grown colonies were replicated onto an M-CM2G solid plate medium containing chloramphenicol (5 μg/mL), and cultivated at 34° C. to obtain chloramphenicol sensitive strains. It was confirmed by Southern hybridization that the vector fell off from chromosome of the obtained chloramphenicol sensitive strains. It was further confirmed that the mutant type HD or the deletion type HD was expressed. It was confirmed by nucleotide sequence determination of chromosomal DNA that the mutation points were introduced into the gene-replaced strains thus obtained.

The HD-M1 gene-replaced strain thus obtained is designated as HDM1 strain, the HD-M2 gene-replaced strain is designated as HDM2 strain, the HD-12 gene-replaced strain is designated as HDM12 strain, and the HD-Δ gene-replaced strain is designated as HDΔ strain.

<2> L-lysine productivity of HD mutant strain and HD deficient strain

The L-lysine productivity was investigated for the HDM1, HDM2 and HDM12 strains as the HD mutant strains, and for the HDΔ strain as the HD deficient strain. These HD mutant strains and HD deficient strain purified by single colony isolation, as well as the AJ12036 strain as the wild strain for HD were respectively cultivated in a flask of 500 mL added with 20 mL of an L-lysine production medium shown below at 31.5° C. for 72 hours. The final OD (OD$_{562}$) and accumulated amount of L-lysine were examined. (L-lysine production medium)

This medium was prepared by dissolving components described below (in 1 L), adjusting pH to 8.0 with KOH, sterilizing at 115° C. for 15 minutes, and then adding 50 g/L of CaCO$_3$ having been sterilized by heat in a dry state.

| Glucose | 100 g |
| (NH$_4$)$_2$SO$_4$ | 55 g |
| KH$_2$PO$_4$ | 1 g |
| MgSO$_4$.7H$_2$O | 1 g |
| d-biotin | 500 μg |
| Thiamin-HCl | 2000 μg |
| FeSO$_4$.7H$_2$O | 0.01 g |

-continued

| | |
|---|---|
| MnSO$_4$·7H$_2$O | 0.01 g |
| Nicotinamide | 5 mg |
| Mamenou (T-N) | 1.05 g |
| GD113 | 0.05 ml |

Figure 5A:
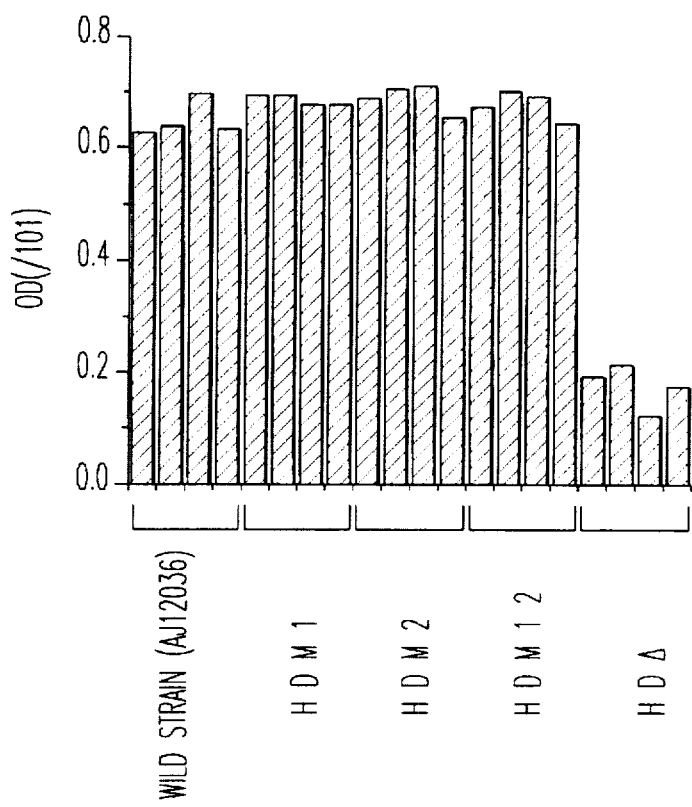
FIG. 5 shows L-lysine productivity and OD after cultivation of HD mutant strain and HD deficient strain.
Figure 5B:
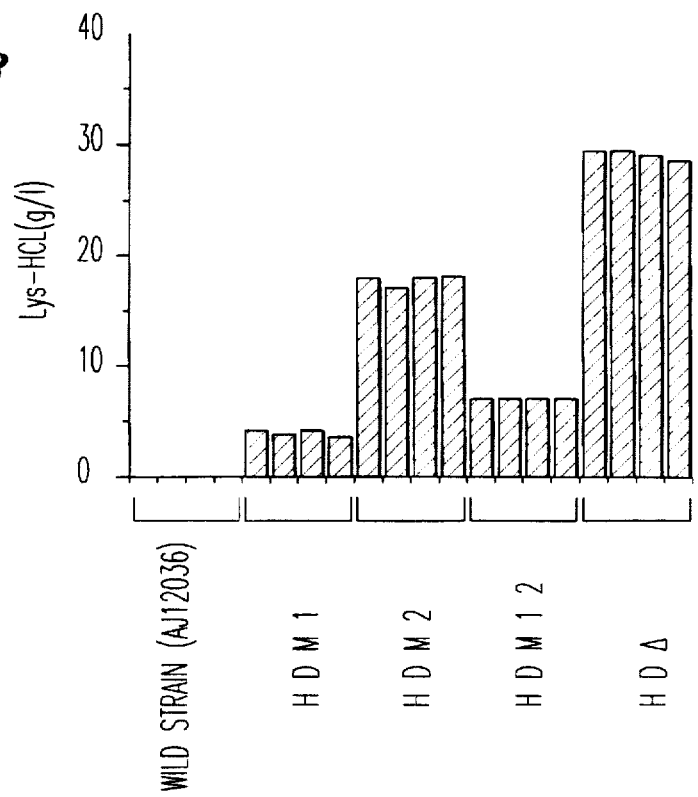

Results are shown in FIG. 5. No remaining sugar was found in any strain. As clarified from the results, accumulation of L-lysine was scarcely observed in AJ12036 strain, while it was about 4 g/l for HDM1 strain, about 17 g/l for HDM2 strain, about 7.5 g/l for HDM12 strain, and about 30 g/l for HDΔ strain. Accumulation of L-lysine was observed in any of the latter strains. Especially the L-lysine productivity was remarkably improved in HDΔ strain. Further, it was clarified that L-lysine was accumulated by introduction of only the mutation point 1 into HD.

HDΔ strain did not grow in a minimum medium or another minimum medium added with L-threonine or L-methionine alone, however, its growth was recovered by addition of L-homoserine, or L-threonine and L-methionine. Any of HDM1, HDM2 and HDM12 strains could grow in a minimum medium containing neither L-threonine nor L-methionine.

*Brevibacterium lactofermentum* HDΔ strain was designated as *Brevibacterium lactofermentum* AJ12846. It has been deposited on Mar. 1, 1994 in National Institute of Bioscience and Human Technology of Agency of Industrial Science and Technology under a deposition number of FERM P-14197, transferred to international deposition based on the Budapest Treaty on Feb. 9, 1995, and deposited under a deposition number of FERM BP-4995.

EXAMPLE 4

Effect of Amplification of AK Gene in HD Mutant Strains and HD Deficient Strain

As described in Example 3, it has been clarified that the L-lysine productivity is improved by introducing the mutant type HD genes and the deletion type HD gene into the wild strain. Further investigation was made for the effect expected by combining AK gene amplification with the mutant type HD genes and the deletion type HD gene.

It is known that AK undergoes concerted inhibition by L-lysine and L-threonine, however, the degree of inhibition is low in the case of the presence of each of them alone. Therefore, since no L-threonine is produced by the HD mutant strain and the HD deficient strain, it is expected that the L-lysine productivity may be also improved by amplification of the wild type AK gene. It is further expected that the L-lysine productivity may be more improved by introducing the gene coding for the mutant type AK obtained in Example 2 which does not undergo inhibition by L-lysine and L-threonine.

In order to investigate such a combined effect of introduction of the mutant type HD gene or the deletion type HD gene and amplification of the AK gene, plasmids containing the AK genes were introduced into the HD mutant strains and the HD deficient strain obtained in Example 3, and the L-lysine productivity was evaluated.

Each of the strains of AJ12036 as a wild strain, HDM1, HDM2 and HDM12 as HD mutant strains, and HDΔ as an HD deficient strain was used as hosts respectively, and transformed with the plasmid (p399AKYB) having the wild type AK gene and Coryne.-ori and the plasmid (p399AK9B) having the mutant type AK. Namely, 5 species of the hosts were transformed with 2 species of the plasmids, and 10 species of transformed strains were obtained in total.

Two strains for each of the transformed strains of AJ12036, HDM1, HDM2, HDM12 and HD A were cultivated by using the aforementioned L-lysine production medium, and the L-lysine productivity was examined. However, the transformed strains harboring the p399AKYB plasmid and the p399AK9B plasmid were cultivated with addition of 10 μg/mL of chloramphenicol to both a medium used for pre-cultivation and the L-lysine production medium. The cultivation was performed with stirring at 31.5° C. for 72 hours in a flask of 500 mL added with 20 mL of the medium.

Figure 6A:
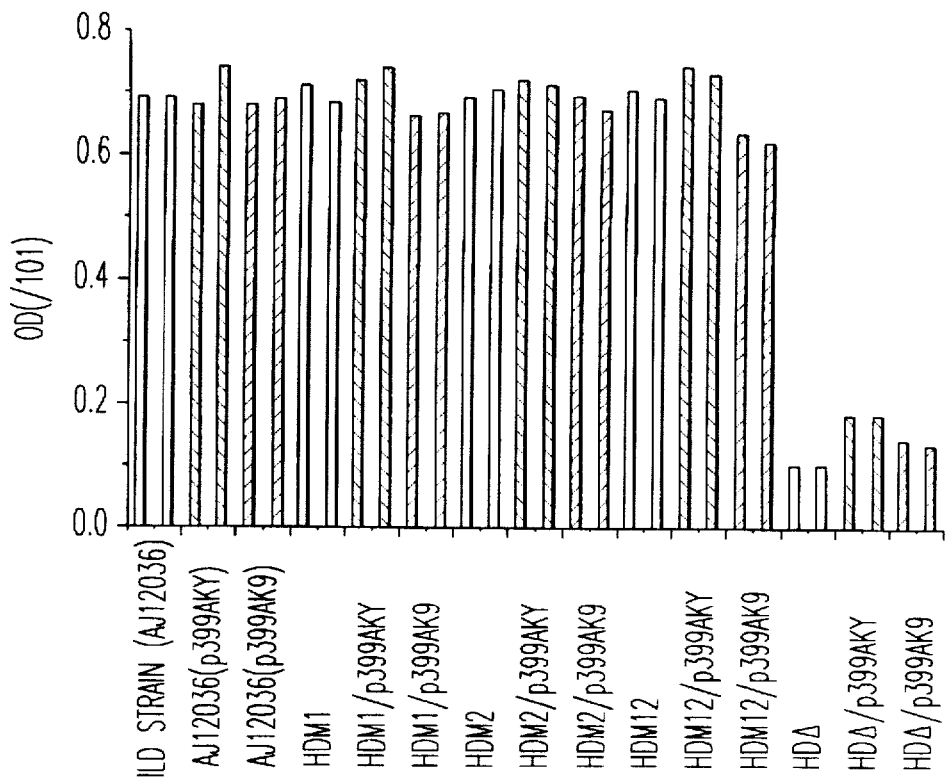
FIG. 6 shows L-lysine productivity and OD after cultivation of HD mutant strain and HD deficient strain in which AK gene is amplified.
Figure 6B:
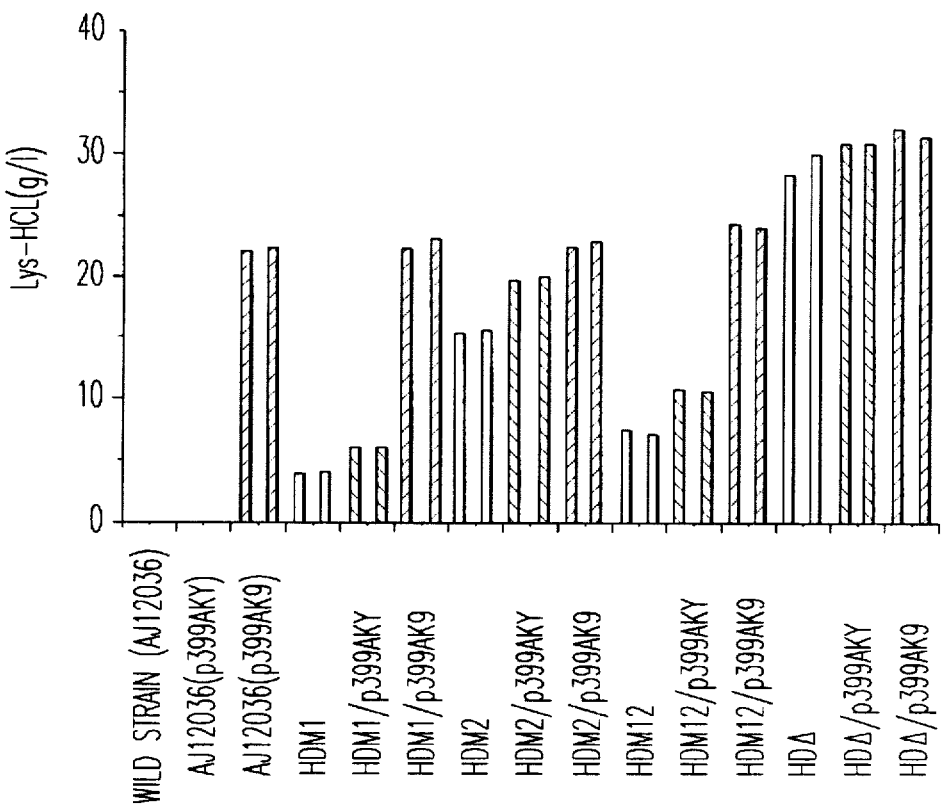

According to the result as shown in FIG. 6, no improvement in L-lysine productivity was observed for the AJ12036 strain even when the wild type AK plasmid was introduced, while increase in accumulated amount of L-lysine was observed for the HD mutant strain and the HD deficient strain owing to the introduction of the wild type AK plasmid. Further, when the mutant type AK plasmid was introduced, the L-lysine productivity was more improved for any of the HD mutant strains and the HD deficient strain as compared with the case of the introduction of the wild type AK plasmid. Furthermore, accumulation of L-lysine in an amount of about 22 g/L was observed even in the case of the AJ12036 strain harboring the wild type HD gene owing to the introduction of the mutant type AK plasmid.

EXAMPLE 5

Effect of Gene Replacement of Mutant Type AK Gene in HD Mutant Strains and HD Deficient Strain <1> Creation of strains replaced with mutant type AK gene and mutant type HD genes, and strain replaced with mutant type AK and deletion type HD gene The effect of combination of HD mutation and HD deficiency with AK gene amplification has been investigated in Example 4. This Example concerns strains created such that the mutant type HD gene or the deletion type HD gene is integrated on chromosome, and the mutant type AK gene is integrated on chromosome, in order to evaluate the L-lysine productivity.

A plasmid for gene replacement for integrating the mutant type AK gene into chromosomal DNA was obtained as follows.

A plasmid pAK9T for replacing the mutant type AK gene was constructed by inserting the temperature-sensitive replication origin (TSori) of *Brevibacterium lactofermentum* into a BamHI site existing at a vector portion of the plasmid p399AK9 obtained in Example 2 (plasmid with the mutant type AK gene fragment originating from *Brevibacterium lactofermentum* AJ3463 strain amplified from chromosome connected to pHSG399).

A strain introduced with the mutant type AK gene and the HD-M1 gene [(AK$^{FBR}$+HDM1) strain] was obtained by integrating the mutant type AK gene by employing the plasmid for replacing the mutant type AK gene pAK9T, using the HDM1 strain obtained in Example 4 as a parent strain. pAK9T was introduced into the HDM1 strain by means of an electric pulse method (Sugimoto et al., Japanese Patent Laid-open No. 2-207791), and obtained transformed strains were cultivated at 25° C. by using an M-CM2G medium until full growth (about 1–2×10$^9$/ml) was achieved. Cultivated bacterial cells were diluted to give 10$^5$ cells per one plate, spread on an M-CM2G solid plate medium containing chloramphenicol (5 μg/mL), and cultivated at 34° C. for 2–7 days to obtain colonies. It was confirmed for obtained colonies that no plasmid was contained in cells.

Further, integration of pAK9T into chromosome was confirmed by Southern hybridization analysis using linear pHSG399 as a probe.

In the strain of chromosomal integration obtained as described above, two fused genes of an AK gene originally existing on the chromosome and the mutant type AK gene are inserted into chromosome in a state of interposing the vector (including TSori). Next, in order to leave only the mutant type AK gene on chromosomal DNA, the wild type AK gene and the vector were allowed to fall off to obtain a strain replaced with the mutant type AK gene. The vector was allowed to fall off as follows.

The strain integrated with the mutant type AK gene was cultivated in an M-CM2G medium containing chloramphenicol (10 μg/mL) at 34° C. until full growth (1–2×10$^9$) was achieved. Cultivated bacterial cells were spread on an M-CM2G solid plate medium containing no chloramphenicol to give 50–200 colonies per one plate, and cultivated at 34° C. Among clones which formed colonies, a strain was selected in which the L-lysine productivity was improved as compared with the HDM1 strain as the parent strain.

In the same manner, a strain having the mutant type AK gene and the HD-M12 gene [(AK$^{FBR}$+HDM12) strain] was selected as a strain with improved L-lysine productivity compared with the HDM12 strain, by performing gene replacement employing pAK9T in the same manner as described above using the HDM12 strain as a parent strain.

On the other hand, a strain introduced with the mutant type AK gene and the HD-M2 gene [(AK$^{FBR}$+HDM2) strain] was obtained by creating an AK$^{FBR}$ strain having the introduced mutant type AK gene as a parent strain by introducing pAK9T into *Brevibacterium lactofermentum* AJ12036 strain, followed by introduction of the HD-M2 gene. Namely, pAK9T was introduced into the AJ12036 strain by means of an electric pulse method (Sugimoto et al., Japanese Patent Laid-open No. 2-207791), and obtained transformed strains were cultivated at 25° C. by using an M-CM2G medium until full growth (about 1–2×10$^9$/ml) was achieved. Cultivated bacterial cells were diluted to give 10$^5$ cells per one plate, spread on an M-CM2G solid plate medium containing chloramphenicol (5 μg/mL), and cultivated at 34° C. for 2–7 days to obtain colonies. It was confirmed for obtained colonies that no plasmid was contained in cells. Further, integration of pAK9T into chromosome was confirmed by Southern hybridization analysis using linear pHSG399 as a probe.

Next, a strain integrated with the mutant type AK gene was cultivated in an M-CM2G medium containing chloramphenicol (10 μg/mL) at 34° C. until full growth (1–2×10$^9$) was achieved. Cultivated bacterial cells were spread on an M-CM2G solid plate medium containing no chloramphenicol to give 50–200 colonies per one plate, and cultivated at 34° C. Grown colonies were replicated onto an M-CM2G solid plate medium containing chloramphenicol (5 μg/mL), and cultivated at 34° C. to obtain a chloramphenicol sensitive strain. It was confirmed by Southern hybridization that the vector fell off from chromosome of the obtained chloramphenicol sensitive strain. It was further confirmed that the mutant type AK was expressed. It was confirmed by nucleotide sequence determination of chromosomal DNA that the gene-replaced strain thus obtained had the introduced mutation point.

The plasmid pTSHDM2 for replacing the HD-M2 gene was introduced into chromosome of the mutant type AK gene-replaced strain (AK$^{FBR}$ strain) thus obtained, by means of the electric pulse method in the same manner as described above, and a gene-replaced strain in which the plasmid fell off was obtained. The gene-replaced strain was selected in accordance with the improvement in L-lysine productivity and sensitivity to L-threonine or L-methionine.

In the same manner, a strain introduced with the mutant type AK gene and the HD-Δ gene [(AK$^{FBR}$+HDΔ)] was obtained by using the mutant type AK gene-replaced strain (AK$^{FBR}$ strain) as a parent strain, performing gene replacement with pTSHDΔ in the same manner as described above, and selecting a clone auxotrophic for L-methionine and L-threonine due to HD deficiency.

For each of the gene-replaced strains obtained as described above, it was finally confirmed by nucleic acid sequence determination of DNA that mutation points were introduced. Further, it was confirmed by Southern hybridization that the plasmid fell off.

<2> Evaluation of L-lysine productivity of strains replaced with mutant type AK gene and mutant type HD genes, and strain replaced with mutant type AK gene and deletion type HD gene The L-lysine productivity was evaluated for the four strains obtained as described above, namely, (AK$^{FBR}$+HDM1), (AK$^{FBR}$+HDM2), (AK$^{FBR}$+HDM12) and (AK$^{FBR}$+HDΔ) strains.

Each of these strains was cultivated at 31.5° C. for 72 hours in a flask of 500 mL added with 20 mL of the aforementioned L-lysine production medium, to measure OD of culture liquid and the amount of accumulated L-lysine after the cultivation.

Figure 7A:
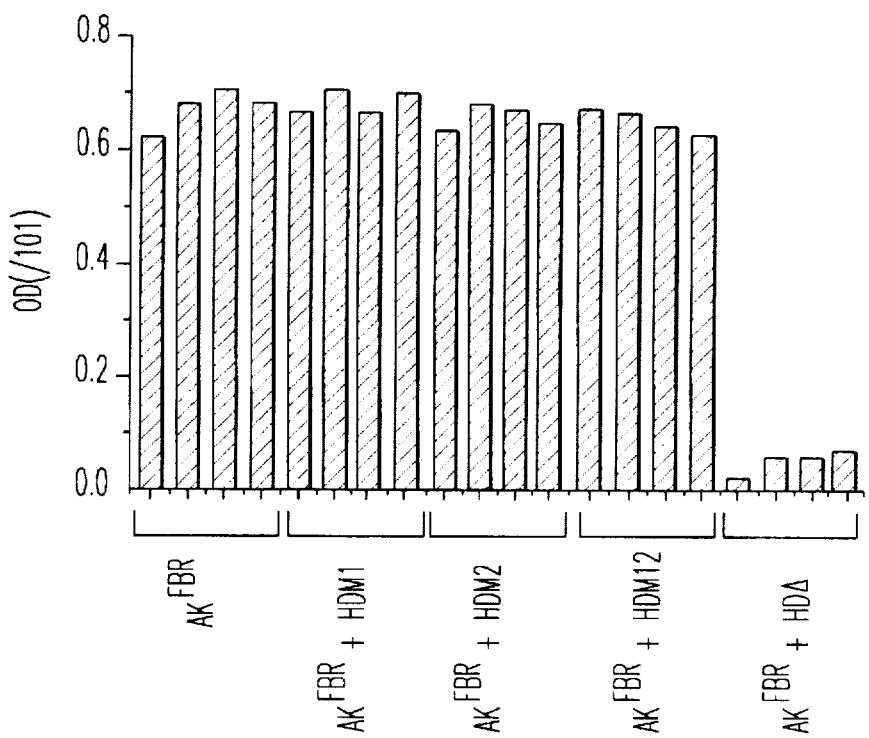
FIG. 7 shows L-lysine productivity and OD after cultivation of HD mutant strain and HD deficient strain in which mutant type AK gene is integrated into chromosome.
Figure 7B:
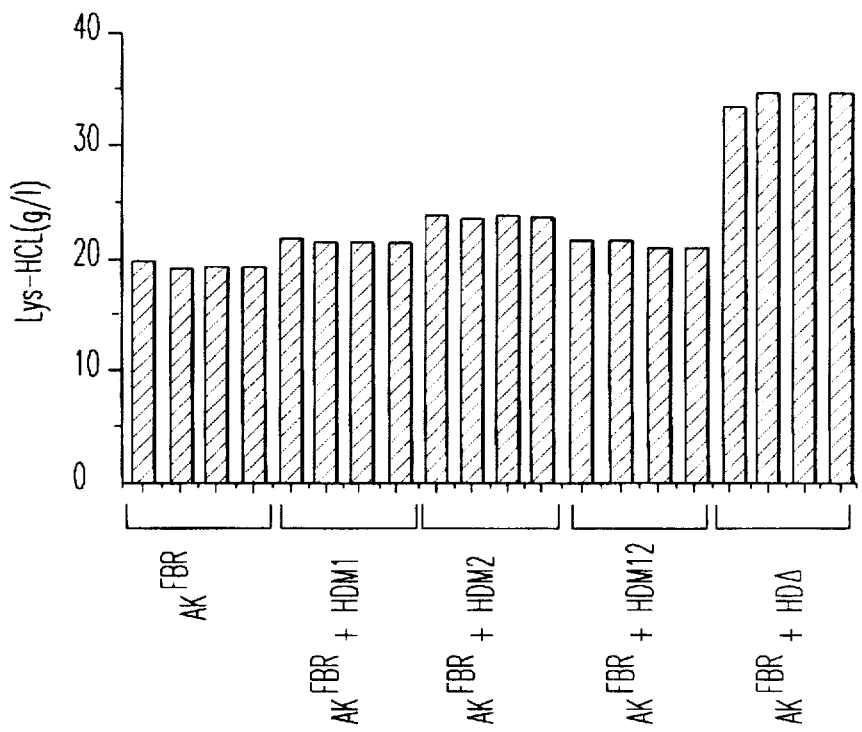

Results are shown in FIG. 7. The amount of produced L-lysine was about 19 g/L for the AK$^{FBR}$ strain, while it was about 21 g/L for the (AK$^{FBR}$+HDM1) strain, about 22 g/L for the (AKF$^{FBR}$+HDM2) strain, about 20 g/L for the (AK$^{FBR}$+HDM12) strain, and about 35 g/L for the (AK$^{FBR}$+HDΔ) strain. It was indicated that the L-lysine productivity was more improved when the mutant type HD genes or the deletion type HD gene was introduced in combination with the mutant type AK gene than when they were introduced alone.

There was little difference in OD of media after completion of the cultivation between the AK$^{FBR}$ strain and any of the (AK$^{FBR}$+HDM1), (AK$^{FBR}$+HDM2) and (AK$^{FBR}$+HDM12) strains. However, OD was more decreased in the case of the (AK$^{FBR}$+HDΔ) strain as compared with the gene-replaced strain with the deletion type HD gene alone. No remaining sugar was found after completion of the cultivation in any of the strains.

The (AK$^{FBR}$+HDM2), (AK$^{FBR}$+HDM12) and (AK$^{FBR}$+HDΔ) strains were designated as AJ12848 (FERM P-14198), AJ12849 (FERM P-14199) and AJ12850 (FERM P-14200), respectively. They have been deposited on Mar. 1, 1994 in National Institute of Bioscience and Human Technology of Agency of Industrial Science and Technology under the deposition numbers described above in the parentheses respectively, transferred to international deposition based on the Budapest Treaty on Feb. 9, 1995, and deposited under deposition numbers of FERM BP-4996, FERM BP-4997 and FERM BP-4998 respectively in this order.

EXAMPLE 6

Measurement of Reverse Mutation Frequency of HD Completely Deficient Strain

The reverse mutation frequency for homoserine auxotrophy was compared between the completely deficient strains of HD (HDΔ and AK$^{FBR}$+HDΔ strains) obtained by the gene replacement on chromosome and an HD deficient strain ATCC 13287 obtained by treating living bacterial cells with N-methyl-N'-nitro-N-nitrosoguanidine (NTG) as an ordinary mutating treatment agent.

The method for comparison was as follows. Stocked bacterial strains were pre-cultivated in a nutrient-rich medium, and inoculated in an L-lysine production medium. After cultivation with stirring for 72 hours, the culture liquids were appropriately diluted. Colonies were formed on an M-CM2G solid plate medium, which were subsequently replicated onto a minimum medium for Brevibacterium containing neither L-methionine nor L-threonine. The ratio of colonies grown on the minimum medium to those grown on the nutrient-rich medium was regarded as a ratio of reverse mutation. When no revertant strain could be observed by using this method, the number of bacterial cells was increased to be applied to the minimum medium, and the number of bacterial cells was changed in accordance with degrees of dilution to be applied to the nutrient-rich medium. The number of bacterial cells applied to the minimum medium was estimated, and the ratio was calculated.

Results of measurement of the reverse mutation frequencies of the aforementioned three strains by means of this method are shown in Table 6. Revertant strains considerably appeared upon completion of the cultivation in the case of the ATCC 13287 strain. On the contrary, no revertant strain was observed at all in the case of the HDΔ and AK$^{FBR}$+HDΔ strains prepared by chromosomal recombination. Further, the HDΔ strain with no occurrence of reverse mutation had a larger amount of produced L-lysine than the ATCC 13287 strain.

TABLE 6

| Bacterial strain | Reverse mutation frequency (%) | Accumulated amount of L-lysine (g/l) |
|---|---|---|
| ATCC 13287 | 40 | 20.0 |
| HDΔ | 0 | 30.0 |
| AK$^{FBR}$ + HDΔ | 0 | 35.0 |

What is claimed is:

1. A DNA fragment encoding a homoserine dehydrogenase originating from a coryneform bacterium, wherein
the amino acid residue corresponding to the 23$^{rd}$ amino acid residue of SEQ ID NO: 4 as measured from the N-terminus is an amino acid residue other than leucine, or
the amino acid residue corresponding to the 104$^{th}$ amino acid residue of SEQ ID NO: 4 as measured from the N-terminus is an amino acid residue other than valine, or
the amino acid residue corresponding to the 23$^{rd}$ amino acid residue of SEQ ID NO: 4 as measured from the N-terminus is an amino acid residue other than leucine, and the amino acid residue corresponding to the 104$^{th}$ amino acid residue of SEQ ID NO: 4 as measured from the N-terminus is an amino acid residue other than valine.

2. A coryneform bacterium which harbors a gene encoding a mutant homoserine dehydrogenase originating from a coryneform bacterium, wherein
the amino acid residue corresponding to the 23$^{rd}$ amino acid residue of SEQ ID NO: 4 as measured from the N-terminus is an amino acid residue other than leucine, or
the amino acid residue corresponding to the 104$^{th}$ amino acid residue of SEQ ID NO: 4 as measured from the N-terminus is an amino acid residue other than valine, or
the amino acid residue corresponding to the 23$^{rd}$ amino acid residue of SEQ ID NO: 4 as measured from the N-terminus is an amino acid residue other than leucine, and the amino acid residue corresponding to the 104$^{th}$ amino acid residue of SEQ ID NO: 4 as measured from the N-terminus is an amino acid residue other than valine.

3. The coryneform bacterium according to claim 2, which is transformed by integrating said gene coding for mutant type homoserine dehydrogenase into chromosomal DNA by way of homologous recombination with a homoserine dehydrogenase gene on a chromosome of the coryneform bacterium.

4. The coryneform bacterium according to claim 2, wherein
the amino acid residue corresponding to the 23$^{rd}$ amino acid residue of SEQ ID NO: 4 as measured from the N-terminus is phenylalanine, or
the amino acid residue corresponding to the 104$^{th}$ amino acid residue of SEQ ID NO: 4 as measured from the N-terminus is isoleucine, or
the amino acid residue corresponding to the 23$^{rd}$ amino acid residue of SEQ ID NO: 4 as measured from the N-terminus is phenylalanine, and the amino acid residue corresponding to the 104$^{th}$ amino acid residue of SEQ ID NO: 4 as measured from the N-terminus is isoleucine.

5. A coryneform bacterium wherein its homoserine dehydrogenase gene is destroyed by integrating a DNA fragment coding for a part of homoserine dehydrogenase originating from a coryneform bacterium into chromosomal DNA by way of homologous recombination with a homoserine dehydrogenase gene on a chromosome of the coryneform bacterium.

6. A coryneform bacterium which harbors in its cells recombinant DNA constructed by ligating an aspartokinase gene originating from a coryneform bacterium with a vector autonomously replicable in cells of coryneform bacteria, wherein its homoserine dehydrogenase gene is destroyed by integrating a DNA fragment coding for a part of homoserine dehydrogenase originating from a coryneform bacterium into its chromosome by way of homologous recombination with a homoserine dehydrogenase gene on the chromosome.

7. The coryneform bacterium according to claim 6, wherein said aspartokinase gene is a gene coding for aspartokinase in which feedback inhibition by L-lysine and L-threonine is substantially desensitized.

8. The coryneform bacterium according to claim 7, wherein the aspartokinase with desensitized feedback inhibition by L-lysine and L-threonine is a mutant aspartokinase wherein the amino acid residue corresponding to the 279$^{th}$ amino acid residue of SEQ ID NO: 9 as measured from the N-terminus is an amino acid residue other than alanine or an acidic amino acid residue, and the amino acid residue corresponding to the 30$^{th}$ amino acid residue of SEQ ID NO: 11 as measured from the N-terminus is an amino acid residue other than alanine or an acidic amino acid residue.

9. A coryneform bacterium which is transformed by integrating, into chromosomal DNA, a gene coding for aspartokinase originating from a coryneform bacterium with desensitized feedback inhibition by L-lysine and L-threonine, wherein its homoserine dehydrogenase gene is destroyed by integrating a DNA fragment coding for a part of homoserine dehydrogenase originating from a coryneform bacterium into its chromosome by way of homologous recombination with a homoserine dehydrogenase gene on the chromosome.

10. The coryneform bacterium according to claim 9, wherein the aspartokinase with desensitized feedback inhibition by L-lysine and L-threonine is a mutant aspartokinase wherein the amino acid residue corresponding to the 279$^{th}$ amino acid residue of SEQ ID NO: 9 as measured from the N-terminus is an amino acid residue other than alanine or an acidic amino acid residue, and the amino acid residue corresponding to the 30$^{th}$ amino acid residue of SEQ ID NO: 11 as measured from the N-terminus is an amino acid residue other than alanine or an acidic amino acid residue.

11. A coryneform bacterium which harbors in its cells recombinant DNA constructed by ligating an aspartokinase gene originating from a coryneform bacterium with a vector autonomously replicable in cells of coryneform bacteria, and is transformed by integrating, into its chromosome, a mutant homoserine dehydrogenase gene encoding a homoserine dehydrogenase originating from a coryneform bacterium wherein, the amino acid residue corresponding to the 23$^{rd}$ amino acid residue of SEQ ID NO: 4 as measured from the N-terminus is an amino acid residue other than leucine, or the amino acid residue corresponding to the 104$^{th}$ amino acid residue of SEQ ID NO: 4 as measured from the N-terminus is an amino acid residue other than valine, or the amino acid residue corresponding to the 23$^{rd}$ amino acid residue of SEQ ID NO: 4 as measured from the N-terminus is an amino acid residue other than leucine, and the amino acid residue corresponding to the 104$^{th}$ amino acid residue of SEQ ID NO: 4 as measured from the N-terminus is an amino acid residue other than valine.

by homologous recombination with a homoserine dehydrogenase gene on the chromosome, and said coryneform bacterium thereby expresses no wild type homoserine dehydrogenase.

12. The coryneform bacterium according to claim 11, wherein said aspartokinase gene is a gene coding for aspartokinase in which feedback inhibition by L-lysine and L-threonine is substantially desensitized.

13. The coryneform bacterium according to claim 12, wherein the aspartokinase with desensitized feedback inhibition by L-lysine and L-threonine is a mutant aspartokinase wherein the amino acid residue corresponding to the 279$^{th}$ amino acid residue of SEQ ID NO: 9 as measured from the N-terminus is an amino acid residue other than alanine or an acidic amino acid residue, and the amino acid residue corresponding to the 30$^{th}$ amino acid residue of SEQ ID NO: 11 as measured from the N-terminus is an amino acid residue other than alanine or an acidic amino acid residue.

14. A coryneform bacterium which is transformed by integrating, into chromosomal DNA, a gene coding for an aspartokinase originating from a coryneform bacterium with desensitized feedback inhibition by L-lysine and L-threonine, and is transformed by integrating, into its chromosome, a mutant homoserine dehydrogenase gene encoding a homoserine dehydrogenase originating from a coryneform bacterium, wherein the amino acid residue corresponding to the 23rd amino acid residue of SEQ ID NO: 4 as measured from the N-terminus is an amino acid residue other than leucine, or the amino acid residue corresponding to the 104th amino acid residue of SEQ ID NO: 4 as measured from the N-terminus is an amino acid residue other than valine, or the amino acid residue corresponding to the 23rd amino acid residue of SEQ ID NO: 4 as measured from the N-terminus is an amino acid residue other than leucine, and the amino acid residue corresponding to the 104th amino acid residue of SEQ ID NO: 4 as measured from the N-terminus is an amino acid residue other than valine.

by homologous recombination with a homoserine dehydrogenase gene on the chromosome, and said coryneform bacterium thereby expresses no wild type homoserine dehydrogenase.

15. The coryneform bacterium according to claim 14, wherein the aspartokinase with desensitized feedback inhibition by L-lysine and L-threonine is a mutant aspartokinase wherein the amino acid residue corresponding to the 279$^{th}$ amino acid residue of SEQ ID NO: 9 as measured from the N-terminus is an amino acid residue other than alanine or an acidic amino acid residue, and the amino acid residue corresponding to the 30$^{th}$ amino acid residue of SEQ ID NO: 11 as measured from the N-terminus is an amino acid residue other than alanine or an acidic amino acid residue.

16. A method of producing L-lysine comprising the steps of cultivating the coryneform bacterium according to claim 2 in an appropriate medium, producing and accumulating L-lysine in a culture thereof, and collecting L-lysine from the culture.

17. The DNA fragment of claim 1, wherein the homoserine dehydrogenase has the sequence of SEQ ID NO: 4, wherein the 23$^{rd}$ amino acid residue as measured from the N-terminus is an amino acid residue other than leucine, or the 104$^{th}$ amino acid residue as measured from the N-terminus is an amino acid residue other than valine, or the 23$^{rd}$ amino acid residue as measured from the N-terminus is an amino acid residue other than leucine, and the 104$^{th}$ amino acid residue as measured from the N-terminus is an amino acid residue other than valine.

18. The DNA fragment of claim 17, wherein the 23$^{rd}$ amino acid residue as measured from the N-terminus is phenylalanine, or the 104$^{th}$ amino acid residue as measured from the N-terminus is isoleucine, or the 23$^{rd}$ amino acid residue as measured from the N-terminus is phenylalanine, and the 104$^{th}$ amino acid residue as measured from the N-terminus is isoleucine.

19. The coryneform bacterium according to claim 2, wherein the homoserine dehydrogenase has the sequence of SEQ ID NO: 4 wherein, the 23$^{rd}$ amino acid residue as measured from the N-terminus is an amino acid residue other than leucine, or the 104$^{th}$ amino acid residue as measured from the N-terminus is an amino acid residue other than valine, or the 23$^{rd}$ amino acid residue as measured from the N-terminus is an amino acid residue other than leucine, and the 104$^{th}$ amino acid residue as measured from the N-terminus is an amino acid residue other than valine.

20. The coryneform bacterium according to claim 19, wherein the 23$^{rd}$ amino acid residue as measured from the N-terminus is phenylalanine, or the 104$^{th}$ amino acid residue as measured from the N-terminus is isoleucine, or the 23$^{rd}$ amino acid residue as measured from the N-terminus is phenylalanine, and the 104$^{th}$ amino acid residue as measured from the N-terminus is isoleucine.

21. The coryneform bacterium according to claim 8, wherein the aspartokinase has an α-subunit having the sequence of SEQ ID NO: 9 and a β-subunit having the sequence of SEQ ID NO: 11, wherein the 279$^{th}$ amino acid residue of SEQ ID NO: 9 as measured from the N-terminus is an amino acid residue other than alanine or an acidic amino acid residue, and the 30$^{rd}$ amino acid residue of SEQ ID NO: 11 as measured from the N-terminus is an amino acid residue other than alanine or an acidic amino acid residue.

22. The coryneform bacterium according to claim 21, wherein the 279$^{th}$ amino acid residue of SEQ ID NO: 9 as measured from the N-terminus is selected from the group consisting of threonine, arginine, cysteine, phenylalanine, proline, serine, tyrosine and valine, and the 30$^{th}$ amino acid residue of SEQ ID NO: 11 as measured from the N-terminus is selected from the group consisting of threonine, arginine, cysteine, phenylalanine, proline, serine, tyrosine and valine.

23. The coryneform bacterium according to claim 10, wherein the aspartokinase has an α-subunit having the sequence of SEQ ID NO: 9 and a β-subunit having the sequence of SEQ ID NO: 11, wherein the 279$^{th}$ amino acid residue of SEQ ID NO: 9 as measured from the N-terminus is an amino acid residue other than alanine or an acidic amino acid residue, and the 30$^{th}$ amino acid residue of SEQ ID NO: 11 as measured from the N-terminus is an amino acid residue other than alanine or an acidic amino acid residue.

24. The coryneform bacterium according to claim 23, wherein the 279$^{th}$ amino acid residue of SEQ ID NO: 9 as measured from the N-terminus is selected from the group consisting of threonine, arginine, cysteine, phenylalanine, proline, serine, tyrosine and valine, and the 30$^{th}$ amino acid residue of SEQ ID NO: 11 as measured from the N-terminus is selected from the group consisting of threonine, arginine, cysteine, phenylalanine, proline, serine, tyrosine and valine.

25. The coryneform bacterium according to claim 13, wherein the aspartokinase has an α-subunit having the sequence of SEQ ID NO: 9 and a β-subunit having the sequence of SEQ ID NO: 11, wherein the 279$^{th}$ amino acid residue of SEQ ID NO: 9 as measured from the N-terminus is an amino acid residue other than alanine or an acidic amino acid residue, and the 30$^{th}$ amino acid residue of SEQ ID NO: 11 as measured from the N-terminus is an amino acid residue other than alanine or an acidic amino acid residue.

26. The coryneform bacterium according to claim 25, wherein the 279$^{th}$ amino acid residue of SEQ ID NO: 9 as measured from the N-terminus is selected from the group consisting of threonine, arginine, cysteine, phenylalanine, proline, serine, tyrosine and valine, and the 30$^{th}$ amino acid residue of SEQ ID NO: 11 as measured from the N-terminus is selected from the group consisting of threonine, arginine, cysteine, phenylalanine, proline, serine, tyrosine and valine.

27. The coryneform bacterium according to claim 15, wherein the aspartokinase has an α-subunit having the sequence of SEQ ID NO: 9 and a β-subunit having the sequence of SEQ ID NO: 11, wherein the 279$^{th}$ amino acid residue of SEQ ID NO: 9 as measured from the N-terminus is an amino acid residue other than alanine or an acidic amino acid residue, and the 30$^{th}$ amino acid residue of SEQ ID NO: 11 as measured from the N-terminus is an amino acid residue other than alanine or an acidic amino acid residue.

28. The coryneform bacterium according to claim 26, wherein the 279$^{th}$ amino acid residue of SEQ ID NO: 9 as measured from the N-terminus is selected from the group consisting of threonine, arginine, cysteine, phenylalanine, proline, serine, tyrosine and valine, and the 30$^{th}$ amino acid residue of SEQ ID NO: 11 as measured from the N-terminus is selected from the group consisting of threonine, arginine, cysteine, phenylalanine, proline, serine, tyrosine and valine.

29. The coryneform bacterium according to claim 11, wherein the homoserine dehydrogenase has the sequence of SEQ ID: 4 wherein, the 23rd amino acid residue as measured from the N-terminus is an amino acid residue other than leucine, or the 104th amino acid residue as measured from the N-terminus is an amino acid residue other than valine, or the 23rd amino acid residue as measured from the N-terminus is an amino acid residue other than leucine, and the 104th amino acid residue as measured from the N-terminus is an amino acid residue other than valine.

30. The coryneform bacterium according to claim 14, wherein the homoserine dehydrogenase has the sequence of SEQ ID: 4 wherein, the 23rd amino acid residue as measured from the N-terminus is an amino acid residue other than leucine, or the 104th amino acid residue as measured from the N-terminus is an amino acid residue other than valine, or the 23rd amino acid residue as measured from the N-terminus is an amino acid residue other than leucine, and the 104th amino acid residue as measured from the N-terminus is an amino acid residue other than valine.

\* \* \* \* \*

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: other..synthetic oligonucleotide ( x i ) SEQUENCE DESCRIPTION: SEQ ID NO:1:

CTGGGAAGGT GAATCGAATT                                                2 0

( 2 ) INFORMATION FOR SEQ ID NO:2:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: other..synthetic oligonucleotide ( x i ) SEQUENCE DESCRIPTION: SEQ ID NO:2:

TCCGAGGTTT GCAGAAGATC                                                2 0

( 2 ) INFORMATION FOR SEQ ID NO:3:

( i ) SEQUENCE CHARACTERISTICS:
        ( A ) LENGTH: 1478
        ( B ) TYPE: nucleic acid
        ( C ) STRANDEDNESS: double
        ( D ) TOPOLOGY: linear ( i i ) MOLECULE TYPE: genomic DNA ( v i ) ORIGINAL SOURCE:
        ( A ) ORGANISM: Brevibacterium lactofermentum
        ( B ) STRAIN: AJ12036

(ix) FEATURE:
   (A) NAME/KEY: CDS
   (B) LOCATION: 89..1423
   (c) IDENTIFICATION METHOD: S (xi) SEQUENCE DESCRIPTION: SEQ ID NO:3:

```
GGTACCCTTT TTGTTTTGGA CACATGTAGG GTGGCCGAAA CAAAGTAATA GGACAACAAC          60

GCTCGACCGC GATTATTTTT GGAGAATC ATG ACC TCA GCA TCT GCC CCA AGC           112
                                Met Thr Ser Ala Ser Ala Pro Ser
                                 1               5

TTT AAC CCC GGC AAG GGT CCC GGC TCA GCA GTC GGA ATT GCC CTT TTA          160
Phe Asn Pro Gly Lys Gly Pro Gly Ser Ala Val Gly Ile Ala Leu Leu
        10              15                  20

GGA TTC GGA ACA GTC GGC ACT GAG GTG ATG CGT CTG ATG ACC GAG TAC          208
Gly Phe Gly Thr Val Gly Thr Glu Val Met Arg Leu Met Thr Glu Tyr
 25              30                  35                  40

GGT GAT GAA CTT GCG CAC CGC ATT GGT GGC CCA CTG GAG GTT CGT GGC          256
Gly Asp Glu Leu Ala His Arg Ile Gly Gly Pro Leu Glu Val Arg Gly
                     45                  50                  55

ATT GCT GTT TCT GAT ATC TCA AAG CCA CGT GAA GGC GTT GCA CCT GAG          304
Ile Ala Val Ser Asp Ile Ser Lys Pro Arg Glu Gly Val Ala Pro Glu
                 60                  65                  70

CTG CTC ACT GAG GAC GCT TTT GCA CTC ATC GAG CGC GAG GAT GTT GAC          352
Leu Leu Thr Glu Asp Ala Phe Ala Leu Ile Glu Arg Glu Asp Val Asp
             75                  80                  85

ATC GTC GTT GAG GTT ATC GGC GGC ATT GAG TAC CCA CGT GAG GTA GTT          400
Ile Val Val Glu Val Ile Gly Gly Ile Glu Tyr Pro Arg Glu Val Val
         90                  95                 100

CTC GCA GCT CTG AAG GCC GGC AAG TCT GTT GTT ACC GCC AAT AAG GCT          448
Leu Ala Ala Leu Lys Ala Gly Lys Ser Val Val Thr Ala Asn Lys Ala
105                 110                 115                 120

CTT GTT GCA GCT CAC TCT GCT GAG CTT GCT GAT GCA GCG GAA GCC GCA          496
Leu Val Ala Ala His Ser Ala Glu Leu Ala Asp Ala Ala Glu Ala Ala
                125                 130                 135

AAC GTT GAC CTG TAC TTC GAG GCT GCT GTT GCA GCC GCA ATT CCA GTG          544
Asn Val Asp Leu Tyr Phe Glu Ala Ala Val Ala Ala Ala Ile Pro Val
            140                 145                 150

GTT GGC CCA CTG CGT CGC TCC CTG GCT GGC GAT CAG ATC CAG TCT GTG          592
Val Gly Pro Leu Arg Arg Ser Leu Ala Gly Asp Gln Ile Gln Ser Val
        155                 160                 165

ATG GGC ATC GTT AAC GGC ACC ACC AAC TTC ATC TTG GAC GCC ATG GAT          640
Met Gly Ile Val Asn Gly Thr Thr Asn Phe Ile Leu Asp Ala Met Asp
170                 175                 180

TCC ACC GGC GCT GAC TAT GCA GAT TCT TTG GCT GAG GCA ACT CGT TTG          688
Ser Thr Gly Ala Asp Tyr Ala Asp Ser Leu Ala Glu Ala Thr Arg Leu
185                 190                 195                 200

GGT TAC GCC GAA GCT GAT CCA ACT GCA GAC GTC GAA GGC CAT GAC GCC          736
Gly Tyr Ala Glu Ala Asp Pro Thr Ala Asp Val Glu Gly His Asp Ala
                205                 210                 215

GCA TCC AAG GCT GCA ATT TTG GCA TCC ATC GCT TTC CAC ACC CGT GTT          784
Ala Ser Lys Ala Ala Ile Leu Ala Ser Ile Ala Phe His Thr Arg Val
            220                 225                 230

ACC GCG GAT GAT GTG TAC TGC GAA GGT ATC AGC AAC ATC AGC GCT GCC          832
Thr Ala Asp Asp Val Tyr Cys Glu Gly Ile Ser Asn Ile Ser Ala Ala
        235                 240                 245

GAC ATT GAG GCA GCA CAG CAG GCA GGC CAC ACC ATC AAG TTG TTG GCC          880
Asp Ile Glu Ala Ala Gln Gln Ala Gly His Thr Ile Lys Leu Leu Ala
250                 255                 260

ATC TGT GAG AAG TTC ACC AAC AAG GAA GGA AAG TCG GCT ATT TCT GCT          928
Ile Cys Glu Lys Phe Thr Asn Lys Glu Gly Lys Ser Ala Ile Ser Ala
265                 270                 275                 280
```

-continued

```
CGC GTG CAC CCG ACT CTA TTA CCT GTG TCC CAC CCA CTG GCG TCG GTA        976
Arg Val His Pro Thr Leu Leu Pro Val Ser His Pro Leu Ala Ser Val
            285                 290                 295

AAC AAG TCC TTT AAT GCA ATC TTT GTT GAA GCA GAA GCA GCT GGT CGC       1024
Asn Lys Ser Phe Asn Ala Ile Phe Val Glu Ala Glu Ala Ala Gly Arg
        300                 305                 310

CTG ATG TTC TAC GGA AAC GGT GCA GGT GGC GCG CCA ACC GCG TCT GCT       1072
Leu Met Phe Tyr Gly Asn Gly Ala Gly Gly Ala Pro Thr Ala Ser Ala
        315                 320                 325

GTG CTT GGC GAC GTC GTT GGT GCC GCA CGA AAC AAG GTG CAC GGT GGC       1120
Val Leu Gly Asp Val Val Gly Ala Ala Arg Asn Lys Val His Gly Gly
        330                 335                 340

CGT GCT CCA GGT GAG TCC ACC TAC GCT AAC CTG CCG ATC GCT GAT TTC       1168
Arg Ala Pro Gly Glu Ser Thr Tyr Ala Asn Leu Pro Ile Ala Asp Phe
345                 350                 355                 360

GGT GAG ACC ACC ACT CGT TAC CAC CTC GAC ATG GAT GTG GAA GAT CGC       1216
Gly Glu Thr Thr Thr Arg Tyr His Leu Asp Met Asp Val Glu Asp Arg
                365                 370                 375

GTG GGC GTT TTG GCT GAA TTG GCT AGC CTG TTC TCT GAG CAA GGA ATC       1264
Val Gly Val Leu Ala Glu Leu Ala Ser Leu Phe Ser Glu Gln Gly Ile
            380                 385                 390

TCC CTG CGT ACA ATC CGA CAG GAA GAG CGC GAT GAT GAT GCA CGT CTG       1312
Ser Leu Arg Thr Ile Arg Gln Glu Glu Arg Asp Asp Asp Ala Arg Leu
        395                 400                 405

ATC GTT GTC ACG CAC TCT GCG CTG GAA TCT GAT CTT TCC CGC ACC GTT       1360
Ile Val Val Thr His Ser Ala Leu Glu Ser Asp Leu Ser Arg Thr Val
        410                 415                 420

GAA CTG CTG AAG GCT AAG CCT GTT GTT AAG GCA ATC AAC AGT GTG ATC       1408
Glu Leu Leu Lys Ala Lys Pro Val Val Lys Ala Ile Asn Ser Val Ile
425                 430                 435                 440

CGC CTC GAA AGG GAC T AATTTACTG ACATGGCAAT TGAACTGAAC GTCGGTCGTA      1464
Arg Leu Glu Arg Asp
                445

AGGTTACCGT CACG                                                       1478
```

( 2 ) INFORMATION FOR SEQ ID NO:4:

( i ) SEQUENCE CHARACTERISTICS:
        ( A ) LENGTH: 445
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Thr Ser Ala Ser Ala Pro Ser Phe Asn Pro Gly Lys Gly Pro Gly
1               5                   10                  15

Ser Ala Val Gly Ile Ala Leu Leu Gly Phe Gly Thr Val Gly Thr Glu
            20                  25                  30

Val Met Arg Leu Met Thr Glu Tyr Gly Asp Glu Leu Ala His Arg Ile
        35                  40                  45

Gly Gly Pro Leu Glu Val Arg Gly Ile Ala Val Ser Asp Ile Ser Lys
    50                  55                  60

Pro Arg Glu Gly Val Ala Pro Glu Leu Leu Thr Glu Asp Ala Phe Ala
65                  70                  75                  80

Leu Ile Glu Arg Glu Asp Val Asp Ile Val Val Glu Val Ile Gly Gly
            85                  90                  95

Ile Glu Tyr Pro Arg Glu Val Val Leu Ala Ala Leu Lys Ala Gly Lys
            100                 105                 110
```

```
Ser  Val  Val  Thr  Ala  Asn  Lys  Ala  Leu  Val  Ala  Ala  His  Ser  Ala  Glu
          115                      120                      125

Leu  Ala  Asp  Ala  Ala  Glu  Ala  Ala  Asn  Val  Asp  Leu  Tyr  Phe  Glu  Ala
     130                      135                      140

Ala  Val  Ala  Ala  Ala  Ile  Pro  Val  Val  Gly  Pro  Leu  Arg  Arg  Ser  Leu
145                      150                      155                      160

Ala  Gly  Asp  Gln  Ile  Gln  Ser  Val  Met  Gly  Ile  Val  Asn  Gly  Thr  Thr
                    165                      170                      175

Asn  Phe  Ile  Leu  Asp  Ala  Met  Asp  Ser  Thr  Gly  Ala  Asp  Tyr  Ala  Asp
               180                      185                      190

Ser  Leu  Ala  Glu  Ala  Thr  Arg  Leu  Gly  Tyr  Ala  Glu  Ala  Asp  Pro  Thr
          195                      200                      205

Ala  Asp  Val  Glu  Gly  His  Asp  Ala  Ala  Ser  Lys  Ala  Ala  Ile  Leu  Ala
     210                      215                      220

Ser  Ile  Ala  Phe  His  Thr  Arg  Val  Thr  Ala  Asp  Asp  Val  Tyr  Cys  Glu
225                      230                      235                      240

Gly  Ile  Ser  Asn  Ile  Ser  Ala  Ala  Asp  Ile  Glu  Ala  Ala  Gln  Gln  Ala
                    245                      250                      255

Gly  His  Thr  Ile  Lys  Leu  Leu  Ala  Ile  Cys  Glu  Lys  Phe  Thr  Asn  Lys
               260                      265                      270

Glu  Gly  Lys  Ser  Ala  Ile  Ser  Ala  Arg  Val  His  Pro  Thr  Leu  Leu  Pro
          275                      280                      285

Val  Ser  His  Pro  Leu  Ala  Ser  Val  Asn  Lys  Ser  Phe  Asn  Ala  Ile  Phe
     290                      295                      300

Val  Glu  Ala  Glu  Ala  Ala  Gly  Arg  Leu  Met  Phe  Tyr  Gly  Asn  Gly  Ala
305                      310                      315                      320

Gly  Gly  Ala  Pro  Thr  Ala  Ser  Ala  Val  Leu  Gly  Asp  Val  Val  Gly  Ala
                    325                      330                      335

Ala  Arg  Asn  Lys  Val  His  Gly  Gly  Arg  Ala  Pro  Gly  Glu  Ser  Thr  Tyr
               340                      345                      350

Ala  Asn  Leu  Pro  Ile  Ala  Asp  Phe  Gly  Glu  Thr  Thr  Thr  Arg  Tyr  His
          355                      360                      365

Leu  Asp  Met  Asp  Val  Glu  Asp  Arg  Val  Gly  Val  Leu  Ala  Glu  Leu  Ala
     370                      375                      380

Ser  Leu  Phe  Ser  Glu  Gln  Gly  Ile  Ser  Leu  Arg  Thr  Ile  Arg  Gln  Glu
385                      390                      395                      400

Glu  Arg  Asp  Asp  Asp  Ala  Arg  Leu  Ile  Val  Val  Thr  His  Ser  Ala  Leu
                    405                      410                      415

Glu  Ser  Asp  Leu  Ser  Arg  Thr  Val  Glu  Leu  Leu  Lys  Ala  Lys  Pro  Val
               420                      425                      430

Val  Lys  Ala  Ile  Asn  Ser  Val  Ile  Arg  Leu  Glu  Arg  Asp
          435                      440                      445
```

( 2 ) INFORMATION FOR SEQ ID NO:5:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) MOLECULE TYPE: other..synthetic oligonucleotide ( x i ) SEQUENCE DESCRIPTION: SEQ ID NO:5:

TCGCGAAGTA GCACCTGTCA CTT 23

( 2 ) INFORMATION FOR SEQ ID NO:6:

( i ) SEQUENCE CHARACTERISTICS:
    ( A ) LENGTH: 21
    ( B ) TYPE: nucleic acid
    ( C ) STRANDEDNESS: single
    ( D ) TOPOLOGY: linear ( i i ) MOLECULE TYPE: other..synthetic oligonucleotide ( x i ) SEQUENCE DESCRIPTION: SEQ ID NO:6:

```
ACGGAATTCA ATCTTACGGC C                                                 21
```

( 2 ) INFORMATION FOR SEQ ID NO:7:

( i ) SEQUENCE CHARACTERISTICS:
        ( A ) LENGTH: 1643
        ( B ) TYPE: nucleic acid
        ( C ) STRANDEDNESS: double
        ( D ) TOPOLOGY: linear ( i i ) MOLECULE TYPE: genomic DNA ( v i ) ORIGINAL SOURCE:
        ( A ) ORGANISM: Corynebacterium glutamicum
        ( B ) STRAIN: ATCC 13869

( x i ) SEQUENCE DESCRIPTION: SEQ ID NO:7:

```
TCGCGAAGTA GCACCTGTCA CTTTTGTCTC AAATATTAAA TCGAATATCA ATATACGGTC     60
TGTTTATTGG AACGCATCCC AGTGGCTGAG ACGCATCCGC TAAAGCCCCA GGAACCCTGT    120
GCAGAAAGAA AACACTCCTC TGGCTAGGTA GACACAGTTT ATAAGGTAG AGTTGAGCGG     180
GTAACTGTCA GCACGTAGAT CGAAAGGTGC ACAAGGTGG CCCTGGTCGT ACAGAAATAT     240
GGCGGTTCCT CGCTTGAGAG TGCGGAACGC ATTAGAAACG TCGCTGAACG GATCGTTGCC    300
ACCAAGAAGG CTGGAAATGA TGTCGTGGTT GTCTGCTCCG CAATGGGAGA CACCACGGAT    360
GAACTTCTAG AACTTGCAGC GGCAGTGAAT CCCGTTCCGC CAGCTCGTGA AATGGATATG    420
CTCCTGACTG CTGGTGAGCG TATTTCTAAC GCTCTCGTCG CCATGGCTAT TGAGTCCCTT    480
GGCGCAGAAG CTCAATCTTT CACTGGCTCT CAGGCTGGTG TGCTCACCAC CGAGCGCCAC    540
GGAAACGCAC GCATTGTTGA CGTCACACCG GGTCGTGTGC GTGAAGCACT CGATGAGGGC    600
AAGATCTGCA TTGTTGCTGG TTTTCAGGGT GTTAATAAAG AAACCCGCGA TGTCACCACG    660
TTGGGTCGTG GTGGTTCTGA CACCACTGCA GTTGCGTTGG CAGCTGCTTT GAACGCTGAT    720
GTGTGTGAGA TTTACTCGGA CGTTGACGGT GTGTATACCG CTGACCCGCG CATCGTTCCT    780
AATGCACAGA AGCTGGAAAA GCTCAGCTTC GAAGAAATGC TGGAACTTGC TGCTGTTGGC    840
TCCAAGATTT TGGTGCTGCG CAGTGTTGAA TACGCTCGTG CATTCAATGT GCCACTTCGC    900
GTACGCTCGT CTTATAGTAA TGATCCCGGC ACTTTGATTG CCGGCTCTAT GGAGGATATT    960
CCTGTGGAAG AAGCAGTCCT TACCGGTGTC GCAACGACA AGTCCGAAGC CAAAGTAACC    1020
GTTCTGGGTA TTTCCGATAA GCCAGGCGAG GCTGCCAAGG TTTTCCGTGC GTTGGCTGAT   1080
GCAGAAATCA ACATTGACAT GGTTCTGCAG AACGTCTCCT CTGTGGAAGA CGGCACCACC   1140
GACATCACGT TCACCTGCCC TCGCGCTGAC GGACGCCGTG CGATGGAGAT CTTGAAGAAG   1200
CTTCAGGTTC AGGGCAACTG GACCAATGTG CTTTACGACG ACCAGGTCGG CAAAGTCTCC   1260
CTCGTGGGTG CTGGCATGAA GTCTCACCCA GGTGTTACCG CAGAGTTCAT GGAAGCTCTG   1320
CGCGATGTCA ACGTGAACAT CGAATTGATT TCCACCTCTG AGATCCGCAT TTCCGTGCTG   1380
ATCCGTGAAG ATGATCTGGA TGCTGCTGCA CGTGCATTGC ATGAGCAGTT CCAGCTGGGC   1440
GGCGAAGACG AAGCCGTCGT TTATGCAGGC ACCGGACGCT AAAGTTTTAA AGGAGTAGTT   1500
```

```
TTACAATGAC CACCATCGCA GTTGTTGGTG CAACCGGCCA GGTCGGCCAG GTTATGCGCA   1560

CCCTTTTGGA AGAGCGCAAT TTCCCAGCTG ACACTGTTCG TTTCTTTGCT TCCCCGCGTT   1620

CCGCAGGCCG TAAGATTGAA TTC                                          1643
```

( 2 ) INFORMATION FOR SEQ ID NO:8:

( i ) SEQUENCE CHARACTERISTICS:
        ( A ) LENGTH: 1643
        ( B ) TYPE: nucleic acid
        ( C ) STRANDEDNESS: double
        ( D ) TOPOLOGY: linear ( i i ) MOLECULE TYPE: genomic DNA ( v i ) ORIGINAL SOURCE:
        ( A ) ORGANISM: Corynebacterium glutamicum
        ( B ) STRAIN: ATCC13869

( i x ) FEATURE:
        ( A ) NAME/KEY: mat peptide
        ( B ) LOCATION: 217..1479
        ( C ) IDENTIFICATION METHOD: S ( x i ) SEQUENCE DESCRIPTION: SEQ ID NO:8:

```
TCGCGAAGTA GCACCTGTCA CTTTTGTCTC AAATATTAAA TCGAATATCA ATATACGGTC    60

TGTTTATTGG AACGCATCCC AGTGGCTGAG ACGCATCCGC TAAAGCCCCA GGAACCCTGT   120

GCAGAAAGAA AACACTCCTC TGGCTAGGTA GACACAGTTT ATAAAGGTAG AGTTGAGCGG   180

GTAACTGTCA GCACGTAGAT CGAAAGGTGC ACAAAG GTG GCC CTG GTC GTA CAG   234
                                        Met Ala Leu Val Val Gln
                                         1               5

AAA TAT GGC GGT TCC TCG CTT GAG AGT GCG GAA CGC ATT AGA AAC GTC   282
Lys Tyr Gly Gly Ser Ser Leu Glu Ser Ala Glu Arg Ile Arg Asn Val
         10              15                  20

GCT GAA CGG ATC GTT GCC ACC AAG AAG GCT GGA AAT GAT GTC GTG GTT   330
Ala Glu Arg Ile Val Ala Thr Lys Lys Ala Gly Asn Asp Val Val Val
        25              30              35

GTC TGC TCC GCA ATG GGA GAC ACC ACG GAT GAA CTT CTA GAA CTT GCA   378
Val Cys Ser Ala Met Gly Asp Thr Thr Asp Glu Leu Leu Glu Leu Ala
    40              45              50

GCG GCA GTG AAT CCC GTT CCG CCA GCT CGT GAA ATG GAT ATG CTC CTG   426
Ala Ala Val Asn Pro Val Pro Pro Ala Arg Glu Met Asp Met Leu Leu
55              60              65                          70

ACT GCT GGT GAG CGT ATT TCT AAC GCT CTC GTC GCC ATG GCT ATT GAG   474
Thr Ala Gly Glu Arg Ile Ser Asn Ala Leu Val Ala Met Ala Ile Glu
            75              80              85

TCC CTT GGC GCA GAA GCT CAA TCT TTC ACT GGC TCT CAG GCT GGT GTG   522
Ser Leu Gly Ala Glu Ala Gln Ser Phe Thr Gly Ser Gln Ala Gly Val
        90              95              100

CTC ACC ACC GAG CGC CAC GGA AAC GCA CGC ATT GTT GAC GTC ACA CCG   570
Leu Thr Thr Glu Arg His Gly Asn Ala Arg Ile Val Asp Val Thr Pro
    105             110             115

GGT CGT GTG CGT GAA GCA CTC GAT GAG GGC AAG ATC TGC ATT GTT GCT   618
Gly Arg Val Arg Glu Ala Leu Asp Glu Gly Lys Ile Cys Ile Val Ala
120             125             130

GGT TTT CAG GGT GTT AAT AAA GAA ACC CGC GAT GTC ACC ACG TTG GGT   666
Gly Phe Gln Gly Val Asn Lys Glu Thr Arg Asp Val Thr Thr Leu Gly
135             140             145             150

CGT GGT GGT TCT GAC ACC ACT GCA GTT GCG TTG GCA GCT GCT TTG AAC   714
Arg Gly Gly Ser Asp Thr Thr Ala Val Ala Leu Ala Ala Ala Leu Asn
                155             160             165

GCT GAT GTG TGT GAG ATT TAC TCG GAC GTT GAC GGT GTG TAT ACC GCT   762
Ala Asp Val Cys Glu Ile Tyr Ser Asp Val Asp Gly Val Tyr Thr Ala
```

-continued

|     | 170 |     |     |     | 175 |     |     |     | 180 |     |     |     |     |     |     |      |
|-----|-----|-----|-----|-----|-----|-----|-----|-----|-----|-----|-----|-----|-----|-----|-----|------|
| GAC | CCG | CGC | ATC | GTT | CCT | AAT | GCA | CAG | AAG | CTG | GAA | AAG | CTC | AGC | TTC | 810  |
| Asp | Pro | Arg | Ile | Val | Pro | Asn | Ala | Gln | Lys | Leu | Glu | Lys | Leu | Ser | Phe |      |
|     |     | 185 |     |     |     |     | 190 |     |     |     |     | 195 |     |     |     |      |
| GAA | GAA | ATG | CTG | GAA | CTT | GCT | GCT | GTT | GGC | TCC | AAG | ATT | TTG | GTG | CTG | 858  |
| Glu | Glu | Met | Leu | Glu | Leu | Ala | Ala | Val | Gly | Ser | Lys | Ile | Leu | Val | Leu |      |
|     | 200 |     |     |     |     | 205 |     |     |     |     | 210 |     |     |     |     |      |
| CGC | AGT | GTT | GAA | TAC | GCT | CGT | GCA | TTC | AAT | GTG | CCA | CTT | CGC | GTA | CGC | 906  |
| Arg | Ser | Val | Glu | Tyr | Ala | Arg | Ala | Phe | Asn | Val | Pro | Leu | Arg | Val | Arg |      |
| 215 |     |     |     |     | 220 |     |     |     |     | 225 |     |     |     |     | 230 |      |
| TCG | TCT | TAT | AGT | AAT | GAT | CCC | GGC | ACT | TTG | ATT | GCC | GGC | TCT | ATG | GAG | 954  |
| Ser | Ser | Tyr | Ser | Asn | Asp | Pro | Gly | Thr | Leu | Ile | Ala | Gly | Ser | Met | Glu |      |
|     |     |     |     | 235 |     |     |     |     | 240 |     |     |     |     | 245 |     |      |
| GAT | ATT | CCT | GTG | GAA | GAA | GCA | GTC | CTT | ACC | GGT | GTC | GCA | ACC | GAC | AAG | 1002 |
| Asp | Ile | Pro | Val | Glu | Glu | Ala | Val | Leu | Thr | Gly | Val | Ala | Thr | Asp | Lys |      |
|     |     |     | 250 |     |     |     |     | 255 |     |     |     |     | 260 |     |     |      |
| TCC | GAA | GCC | AAA | GTA | ACC | GTT | CTG | GGT | ATT | TCC | GAT | AAG | CCA | GGC | GAG | 1050 |
| Ser | Glu | Ala | Lys | Val | Thr | Val | Leu | Gly | Ile | Ser | Asp | Lys | Pro | Gly | Glu |      |
|     | 265 |     |     |     |     | 270 |     |     |     |     | 275 |     |     |     |     |      |
| GCT | GCC | AAG | GTT | TTC | CGT | GCG | TTG | GCT | GAT | GCA | GAA | ATC | AAC | ATT | GAC | 1098 |
| Ala | Ala | Lys | Val | Phe | Arg | Ala | Leu | Ala | Asp | Ala | Glu | Ile | Asn | Ile | Asp |      |
| 280 |     |     |     |     |     | 285 |     |     |     |     | 290 |     |     |     |     |      |
| ATG | GTT | CTG | CAG | AAC | GTC | TCC | TCT | GTG | GAA | GAC | GGC | ACC | ACC | GAC | ATC | 1146 |
| Met | Val | Leu | Gln | Asn | Val | Ser | Ser | Val | Glu | Asp | Gly | Thr | Thr | Asp | Ile |      |
| 295 |     |     |     |     | 300 |     |     |     |     | 305 |     |     |     |     | 310 |      |
| ACG | TTC | ACC | TGC | CCT | CGC | GCT | GAC | GGA | CGC | CGT | GCG | ATG | GAG | ATC | TTG | 1194 |
| Thr | Phe | Thr | Cys | Pro | Arg | Ala | Asp | Gly | Arg | Arg | Ala | Met | Glu | Ile | Leu |      |
|     |     |     |     | 315 |     |     |     |     | 320 |     |     |     |     | 325 |     |      |
| AAG | AAG | CTT | CAG | GTT | CAG | GGC | AAC | TGG | ACC | AAT | GTG | CTT | TAC | GAC | GAC | 1242 |
| Lys | Lys | Leu | Gln | Val | Gln | Gly | Asn | Trp | Thr | Asn | Val | Leu | Tyr | Asp | Asp |      |
|     |     |     | 330 |     |     |     |     | 335 |     |     |     |     | 340 |     |     |      |
| CAG | GTC | GGC | AAA | GTC | TCC | CTC | GTG | GGT | GCT | GGC | ATG | AAG | TCT | CAC | CCA | 1290 |
| Gln | Val | Gly | Lys | Val | Ser | Leu | Val | Gly | Ala | Gly | Met | Lys | Ser | His | Pro |      |
|     |     | 345 |     |     |     |     | 350 |     |     |     |     | 355 |     |     |     |      |
| GGT | GTT | ACC | GCA | GAG | TTC | ATG | GAA | GCT | CTG | CGC | GAT | GTC | AAC | GTG | AAC | 1338 |
| Gly | Val | Thr | Ala | Glu | Phe | Met | Glu | Ala | Leu | Arg | Asp | Val | Asn | Val | Asn |      |
|     | 360 |     |     |     |     | 365 |     |     |     |     | 370 |     |     |     |     |      |
| ATC | GAA | TTG | ATT | TCC | ACC | TCT | GAG | ATC | CGC | ATT | TCC | GTG | CTG | ATC | CGT | 1386 |
| Ile | Glu | Leu | Ile | Ser | Thr | Ser | Glu | Ile | Arg | Ile | Ser | Val | Leu | Ile | Arg |      |
| 375 |     |     |     |     | 380 |     |     |     |     | 385 |     |     |     |     | 390 |      |
| GAA | GAT | GAT | CTG | GAT | GCT | GCT | GCA | CGT | GCA | TTG | CAT | GAG | CAG | TTC | CAG | 1434 |
| Glu | Asp | Asp | Leu | Asp | Ala | Ala | Ala | Arg | Ala | Leu | His | Glu | Gln | Phe | Gln |      |
|     |     |     |     | 395 |     |     |     |     | 400 |     |     |     |     | 405 |     |      |
| CTG | GGC | GGC | GAA | GAC | GAA | GCC | GTC | GTT | TAT | GCA | GGC | ACC | GGA | CGC | TAA | 1482 |
| Leu | Gly | Gly | Glu | Asp | Glu | Ala | Val | Val | Tyr | Ala | Gly | Thr | Gly | Arg |     |      |
|     |     || 410 |     |     |     |     | 415 |     |     |     | 420 | 421 |     |     |      |

AGTTTAAAG GAGTAGTTTT ACAATGACCA CCATCGCAGT TGTTGGTGCA ACCGGCCAGG    1542

TCGGCCAGGT TATGCGCACC CTTTTGGAAG AGCGCAATTT CCCAGCTGAC ACTGTTCGTT    1602

TCTTTGCTTC CCCGCGTTCC GCAGGCCGTA AGATTGAATT C                        1643

( 2 ) INFORMATION FOR SEQ ID NO:9:

( i ) SEQUENCE CHARACTERISTICS:
      ( A ) LENGTH: 421
      ( B ) TYPE: amino acid
      ( D ) TOPOLOGY: linear ( i i ) MOLECULE TYPE: protein ( x i ) SEQUENCE DESCRIPTION: SEQ ID NO:9:

```
Met Ala Leu Val Val Gln Lys Tyr Gly Gly Ser Ser Leu Glu Ser Ala
 1            5                   10                  15
Glu Arg Ile Arg Asn Val Ala Glu Arg Ile Val Ala Thr Lys Lys Ala
             20                  25                  30
Gly Asn Asp Val Val Val Val Cys Ser Ala Met Gly Asp Thr Thr Asp
             35                  40                  45
Glu Leu Leu Glu Leu Ala Ala Ala Val Asn Pro Val Pro Pro Ala Arg
     50                  55                  60
Glu Met Asp Met Leu Leu Thr Ala Gly Glu Arg Ile Ser Asn Ala Leu
 65                  70                  75                  80
Val Ala Met Ala Ile Glu Ser Leu Gly Ala Glu Ala Gln Ser Phe Thr
                 85                  90                  95
Gly Ser Gln Ala Gly Val Leu Thr Thr Glu Arg His Gly Asn Ala Arg
             100                 105                 110
Ile Val Asp Val Thr Pro Gly Arg Val Arg Glu Ala Leu Asp Glu Gly
             115                 120                 125
Lys Ile Cys Ile Val Ala Gly Phe Gln Gly Val Asn Lys Glu Thr Arg
     130                 135                 140
Asp Val Thr Thr Leu Gly Arg Gly Gly Ser Asp Thr Thr Ala Val Ala
145                 150                 155                 160
Leu Ala Ala Ala Leu Asn Ala Asp Val Cys Glu Ile Tyr Ser Asp Val
                 165                 170                 175
Asp Gly Val Tyr Thr Ala Asp Pro Arg Ile Val Pro Asn Ala Gln Lys
             180                 185                 190
Leu Glu Lys Leu Ser Phe Glu Glu Met Leu Glu Leu Ala Ala Val Gly
     195                 200                 205
Ser Lys Ile Leu Val Leu Arg Ser Val Glu Tyr Ala Arg Ala Phe Asn
210                 215                 220
Val Pro Leu Arg Val Arg Ser Ser Tyr Ser Asn Asp Pro Gly Thr Leu
225                 230                 235                 240
Ile Ala Gly Ser Met Glu Asp Ile Pro Val Glu Glu Ala Val Leu Thr
             245                 250                 255
Gly Val Ala Thr Asp Lys Ser Glu Ala Lys Val Thr Val Leu Gly Ile
             260                 265                 270
Ser Asp Lys Pro Gly Glu Ala Ala Lys Val Phe Arg Ala Leu Ala Asp
     275                 280                 285
Ala Glu Ile Asn Ile Asp Met Val Leu Gln Asn Val Ser Ser Val Glu
     290                 295                 300
Asp Gly Thr Thr Asp Ile Thr Phe Thr Cys Pro Arg Ala Asp Gly Arg
305                 310                 315                 320
Arg Ala Met Glu Ile Leu Lys Lys Leu Gln Val Gln Gly Asn Trp Thr
                 325                 330                 335
Asn Val Leu Tyr Asp Asp Gln Val Gly Lys Val Ser Leu Val Gly Ala
             340                 345                 350
Gly Met Lys Ser His Pro Gly Val Thr Ala Glu Phe Met Glu Ala Leu
         355                 360                 365
Arg Asp Val Asn Val Asn Ile Glu Leu Ile Ser Thr Ser Glu Ile Arg
     370                 375                 380
Ile Ser Val Leu Ile Arg Glu Asp Asp Leu Asp Ala Ala Ala Arg Ala
385                 390                 395                 400
Leu His Glu Gln Phe Gln Leu Gly Gly Glu Asp Glu Ala Val Val Tyr
                 405                 410                 415
Ala Gly Thr Gly Arg
                 420
```

( 2 ) INFORMATION FOR SEQ ID NO:10:

( i ) SEQUENCE CHARACTERISTICS:
        ( A ) LENGTH: 1643
        ( B ) TYPE: nucleic acid
        ( C ) STRANDEDNESS: double
        ( D ) TOPOLOGY: linear ( i i ) MOLECULE TYPE: genomic DNA ( v i ) ORIGINAL SOURCE:
        ( A ) ORGANISM: Corynebacterium glutamicum
        ( B ) STRAIN: ATCC13869

( i x ) FEATURE:
        ( A ) NAME/KEY: mat peptide
        ( B ) LOCATION: 964..1479
        ( c ) IDENTIFICATION METHOD: S ( x i ) SEQUENCE DESCRIPTION: SEQ ID NO:10:

```
TCGCGAAGTA  GCACCTGTCA  CTTTTGTCTC  AAATATTAAA  TCGAATATCA  ATATACGGTC      60
TGTTTATTGG  AACGCATCCC  AGTGGCTGAG  ACGCATCCGC  TAAAGCCCCA  GGAACCCTGT     120
GCAGAAAGAA  AACACTCCTC  TGGCTAGGTA  GACACAGTTT  ATAAAGGTAG  AGTTGAGCGG     180
GTAACTGTCA  GCACGTAGAT  CGAAAGGTGC  ACAAAGGTGG  CCCTGGTCGT  ACAGAAATAT     240
GGCGGTTCCT  CGCTTGAGAG  TGCGGAACGC  ATTAGAAACG  TCGCTGAACG  GATCGTTGCC     300
ACCAAGAAGG  CTGGAAATGA  TGTCGTGGTT  GTCTGCTCCG  CAATGGGAGA  CACCACGGAT     360
GAACTTCTAG  AACTTGCAGC  GGCAGTGAAT  CCCGTTCCGC  CAGCTCGTGA  AATGGATATG     420
CTCCTGACTG  CTGGTGAGCG  TATTTCTAAC  GCTCTCGTCG  CCATGGCTAT  TGAGTCCCTT     480
GGCGCAGAAG  CTCAATCTTT  CACTGGCTCT  CAGGCTGGTG  TGCTCACCAC  CGAGCGCCAC     540
GGAAACGCAC  GCATTGTTGA  CGTCACACCG  GGTCGTGTGC  GTGAAGCACT  CGATGAGGGC     600
AAGATCTGCA  TTGTTGCTGG  TTTTCAGGGT  GTTAATAAAG  AAACCCGCGA  TGTCACCACG     660
TTGGGTCGTG  GTGGTTCTGA  CACCACTGCA  GTTGCGTTGG  CAGCTGCTTT  GAACGCTGAT     720
GTGTGTGAGA  TTTACTCGGA  CGTTGACGGT  GTGTATACCG  CTGACCCGCG  CATCGTTCCT     780
AATGCACAGA  AGCTGGAAAA  GCTCAGCTTC  GAAGAAATGC  TGGAACTTGC  TGCTGTTGGC     840
TCCAAGATTT  TGGTGCTGCG  CAGTGTTGAA  TACGCTCGTG  CATTCAATGT  GCCACTTCGC     900
GTACGCTCGT  CTTATAGTAA  TGATCCCGGC  ACTTTGATTG  CCGGCTCTAT  GGAGGATATT     960

CCT  GTG GAA GAA GCA GTC CTT ACC GGT GTC GCA ACC GAC AAG TCC GAA         1008
     Met Glu Glu Ala Val Leu Thr Gly Val Ala Thr Asp Lys Ser Glu
      1               5                  10                  15

GCC AAA GTA ACC GTT CTG GGT ATT TCC GAT AAG CCA GGC GAG GCT GCC         1056
Ala Lys Val Thr Val Leu Gly Ile Ser Asp Lys Pro Gly Glu Ala Ala
              20                  25                  30

AAG GTT TTC CGT GCG TTG GCT GAT GCA GAA ATC AAC ATT GAC ATG GTT         1104
Lys Val Phe Arg Ala Leu Ala Asp Ala Glu Ile Asn Ile Asp Met Val
          35                  40                  45

CTG CAG AAC GTC TCC TCT GTG GAA GAC GGC ACC ACC GAC ATC ACG TTC         1152
Leu Gln Asn Val Ser Ser Val Glu Asp Gly Thr Thr Asp Ile Thr Phe
      50                  55                  60

ACC TGC CCT CGC GCT GAC GGA CGC CGT GCG ATG GAG ATC TTG AAG AAG         1200
Thr Cys Pro Arg Ala Asp Gly Arg Arg Ala Met Glu Ile Leu Lys Lys
  65                  70                  75

CTT CAG GTT CAG GGC AAC TGG ACC AAT GTG CTT TAC GAC GAC CAG GTC         1248
Leu Gln Val Gln Gly Asn Trp Thr Asn Val Leu Tyr Asp Asp Gln Val
 80                  85                  90                  95

GGC AAA GTC TCC CTC GTG GGT GCT GGC ATG AAG TCT CAC CCA GGT GTT         1296
```

```
        Gly  Lys  Val  Ser  Leu  Val  Gly  Ala  Gly  Met  Lys  Ser  His  Pro  Gly  Val
                       100                      105                      110

ACC  GCA  GAG  TTC  ATG  GAA  GCT  CTG  CGC  GAT  GTC  AAC  GTG  AAC  ATC  GAA              1344
Thr  Ala  Glu  Phe  Met  Glu  Ala  Leu  Arg  Asp  Val  Asn  Val  Asn  Ile  Glu
               115                      120                      125

TTG  ATT  TCC  ACC  TCT  GAG  ATC  CGC  ATT  TCC  GTG  CTG  ATC  CGT  GAA  GAT              1392
Leu  Ile  Ser  Thr  Ser  Glu  Ile  Arg  Ile  Ser  Val  Leu  Ile  Arg  Glu  Asp
          130                      135                      140

GAT  CTG  GAT  GCT  GCT  GCA  CGT  GCA  TTG  CAT  GAG  CAG  TTC  CAG  CTG  GGC              1440
Asp  Leu  Asp  Ala  Ala  Ala  Arg  Ala  Leu  His  Glu  Gln  Phe  Gln  Leu  Gly
     145                      150                      155

GGC  GAA  GAC  GAA  GCC  GTC  GTT  TAT  GCA  GGC  ACC  GGA  CGC  TAAAGTTTAA                  1490
Gly  Glu  Asp  Glu  Ala  Val  Val  Tyr  Ala  Gly  Thr  Gly  Arg
160                      165                      170       172

AGGAGTAGTT  TTACAATGAC  CACCATCGCA  GTTGTTGGTG  CAACCGGCCA  GGTCGGCCAG                       1550

GTTATGCGCA  CCCTTTTGGA  AGAGCGCAAT  TCCCAGCTG  ACACTGTTCG  TTTCTTTGCT                        1610

TCCCCGCGTT  CCGCAGGCCG  TAAGATTGAA  TTC                                                      1643
```

( 2 ) INFORMATION FOR SEQ ID NO:11:

( i ) SEQUENCE CHARACTERISTICS:
        ( A ) LENGTH: 172
        ( B ) TYPE: amino acid
        ( D ) TOPOLOGY: linear ( i i ) MOLECULE TYPE: protein ( x i ) SEQUENCE DESCRIPTION: SEQ ID NO:11:

```
        Met  Glu  Glu  Ala  Val  Leu  Thr  Gly  Val  Ala  Thr  Asp  Lys  Ser  Glu  Ala
        1                   5                        10                      15

Lys  Val  Thr  Val  Leu  Gly  Ile  Ser  Asp  Lys  Pro  Gly  Glu  Ala  Ala  Lys
                       20                        25                      30

Val  Phe  Arg  Ala  Leu  Ala  Asp  Ala  Glu  Ile  Asn  Ile  Asp  Met  Val  Leu
                  35                        40                      45

Gln  Asn  Val  Ser  Ser  Val  Glu  Asp  Gly  Thr  Thr  Asp  Ile  Thr  Phe  Thr
             50                        55                      60

Cys  Pro  Arg  Ala  Asp  Gly  Arg  Arg  Ala  Met  Glu  Ile  Leu  Lys  Lys  Leu
        65                       70                       75                      80

Gln  Val  Gln  Gly  Asn  Trp  Thr  Asn  Val  Leu  Tyr  Asp  Asp  Gln  Val  Gly
                            85                      90                       95

Lys  Val  Ser  Leu  Val  Gly  Ala  Gly  Met  Lys  Ser  His  Pro  Gly  Val  Thr
                       100                      105                      110

Ala  Glu  Phe  Met  Glu  Ala  Leu  Arg  Asp  Val  Asn  Val  Asn  Ile  Glu  Leu
                  115                      120                      125

Ile  Ser  Thr  Ser  Glu  Ile  Arg  Ile  Ser  Val  Leu  Ile  Arg  Glu  Asp  Asp
             130                      135                      140

Leu  Asp  Ala  Ala  Ala  Arg  Ala  Leu  His  Glu  Gln  Phe  Gln  Leu  Gly  Gly
        145                      150                      155                      160

Glu  Asp  Glu  Ala  Val  Val  Tyr  Ala  Gly  Thr  Gly  Arg
                            165                      170
```

( 2 ) INFORMATION FOR SEQ ID NO:12:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) MOLECULE TYPE: other..synthetic oligonucleotide ( x i ) SEQUENCE DESCRIPTION: SEQ ID NO:12:

GCCAGGCGAG CGTGCCAAGG TTT 23

( 2 ) INFORMATION FOR SEQ ID NO:13:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) MOLECULE TYPE: other..synthetic oligonucleotide ( x i ) SEQUENCE DESCRIPTION: SEQ ID NO:13:

GCCAGGCGAG GATGCCAAGG TTT 23

( 2 ) INFORMATION FOR SEQ ID NO:14:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) MOLECULE TYPE: other..synthetic oligonucleotide ( x i ) SEQUENCE DESCRIPTION: SEQ ID NO:14:

GCCAGGCGAG TGTGCCAAGG TTT 23

( 2 ) INFORMATION FOR SEQ ID NO:15:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) MOLECULE TYPE: other..synthetic oligonucleotide ( x i ) SEQUENCE DESCRIPTION: SEQ ID NO:15:

GCCAGGCGAG TTTGCCAAGG TTT 23

( 2 ) INFORMATION FOR SEQ ID NO:16:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) MOLECULE TYPE: other..synthetic oligonucleotide ( x i ) SEQUENCE DESCRIPTION: SEQ ID NO:16:

GCCAGGCGAG CCTGCCAAGG TTT 23

( 2 ) INFORMATION FOR SEQ ID NO:17:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) MOLECULE TYPE: other..synthetic oligonucleotide ( x i ) SEQUENCE DESCRIPTION: SEQ ID NO:17:

GCCAGGCGAG TCTGCCAAGG TTT 23

( 2 ) INFORMATION FOR SEQ ID NO:18:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) MOLECULE TYPE: other..synthetic oligonucleotide ( x i ) SEQUENCE DESCRIPTION: SEQ ID NO:18:

GCCAGGCGAG TATGCCAAGG TTT                                                23

( 2 ) INFORMATION FOR SEQ ID NO:19:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) MOLECULE TYPE: other..synthetic oligonucleotide ( x i ) SEQUENCE DESCRIPTION: SEQ ID NO:19:

GCCAGGCGAG GTTGCCAAGG TTT                                                23

( 2 ) INFORMATION FOR SEQ ID NO: 20:

( i ) SEQUENCE CHARACTERISTICS:
        ( A ) LENGTH: 433 amino acids
        ( B ) TYPE: amino acid
        ( D ) TOPOLOGY: linear ( x i ) SEQUENCE DESCRIPTION: SEQ ID NO: 20:

```
Met   Lys   Ala   Ile   Arg   Val   Gly   Leu   Leu   Gly   Leu   Gly   Thr   Val   Gly   Ser
 1                       5                        10                             15

Gly   Val   Val   Lys   Ile   Ile   Gln   Asp   His   Gln   Asp   Lys   Leu   Met   His   Gln
                   20                         25                         30

Val   Gly   Cys   Pro   Val   Thr   Ile   Lys   Lys   Val   Leu   Val   Lys   Asp   Leu   Glu
             35                         40                         45

Lys   Lys   Arg   Glu   Val   Asp   Leu   Pro   Lys   Glu   Val   Leu   Thr   Thr   Glu   Val
      50                         55                         60

Tyr   Asp   Val   Ile   Asp   Asp   Pro   Asp   Val   Asp   Val   Val   Ile   Glu   Val   Ile
65                         70                         75                         80

Gly   Gly   Val   Glu   Gln   Thr   Lys   Gln   Tyr   Leu   Val   Asp   Ala   Leu   Arg   Ser
                         85                         90                         95

Lys   Lys   His   Val   Val   Thr   Ala   Asn   Lys   Asp   Leu   Met   Ala   Val   Tyr   Gly
                  100                        105                        110

Ser   Glu   Leu   Leu   Ala   Glu   Ala   Lys   Glu   Asn   Gly   Cys   Asp   Ile   Tyr   Phe
            115                        120                        125

Glu   Ala   Ser   Val   Ala   Gly   Gly   Ile   Pro   Ile   Leu   Arg   Thr   Leu   Glu   Glu
      130                        135                        140

Gly   Leu   Ser   Ser   Asp   Arg   Ile   Thr   Lys   Met   Met   Gly   Ile   Val   Asn   Gly
145                        150                        155                        160

Thr   Thr   Asn   Phe   Ile   Leu   Thr   Lys   Met   Ile   Lys   Glu   Lys   Ser   Pro   Tyr
                        165                        170                        175

Glu   Glu   Val   Leu   Lys   Glu   Ala   Gln   Asp   Leu   Gly   Phe   Ala   Glu   Ala   Asp
                  180                        185                        190

Pro   Thr   Ser   Asp   Val   Glu   Gly   Leu   Asp   Ala   Ala   Arg   Lys   Met   Ala   Ile
            195                        200                        205

Leu   Ala   Arg   Leu   Gly   Phe   Ser   Met   Asn   Val   Asp   Leu   Glu   Asp   Val   Lys
```

-continued

```
              210                            215                            220
Val  Lys  Gly  Ile  Ser  Gln  Ile  Thr  Asp  Glu  Asp  Leu  Ser  Phe  Ser  Lys
225                      230                      235                          240

Arg  Leu  Gly  Tyr  Thr  Met  Lys  Leu  Ile  Gly  Ile  Ala  Gln  Arg  Asp  Gly
                    245                      250                          255

Ser  Lys  Ile  Glu  Val  Ser  Val  Gln  Pro  Thr  Leu  Leu  Pro  Asp  His  His
               260                      265                      270

Pro  Leu  Ser  Ala  Val  His  Asn  Glu  Phe  Asn  Ala  Val  Tyr  Val  Tyr  Gly
          275                      280                      285

Glu  Ala  Val  Gly  Glu  Thr  Met  Phe  Tyr  Gly  Pro  Gly  Ala  Gly  Ser  Met
290                      295                      300

Pro  Thr  Ala  Thr  Ser  Val  Val  Ser  Asp  Leu  Val  Ala  Val  Met  Lys  Asn
305                      310                      315                          320

Met  Arg  Leu  Gly  Val  Thr  Gly  Asn  Ser  Phe  Val  Gly  Pro  Gln  Tyr  Glu
                    325                      330                          335

Lys  Asn  Met  Lys  Ser  Pro  Ser  Asp  Ile  Tyr  Ala  Gln  Gln  Phe  Leu  Arg
               340                      345                      350

Ile  His  Val  Lys  Asp  Glu  Val  Gly  Ser  Phe  Ser  Lys  Ile  Thr  Ser  Val
          355                      360                      365

Phe  Ser  Glu  Arg  Gly  Val  Ser  Phe  Glu  Lys  Ile  Leu  Gln  Leu  Pro  Ile
370                      375                      380

Lys  Gly  His  Asp  Glu  Leu  Ala  Glu  Ile  Val  Ile  Val  Thr  His  His  Thr
385                      390                      395                          400

Ser  Glu  Ala  Asp  Phe  Ser  Asp  Ile  Leu  Gln  Asn  Leu  Asn  Asp  Leu  Glu
               405                      410                      415

Val  Val  Gln  Glu  Val  Lys  Ser  Thr  Tyr  Arg  Val  Glu  Gly  Asn  Gly  Trp
          420                      425                      430

Ser
```

(2) INFORMATION FOR SEQ ID NO: 21:

(i) SEQUENCE CHARACTERISTICS:
      (A) LENGTH: 369 amino acids
      (B) TYPE: amino acid
      (D) TOPOLOGY: linear (x i) SEQUENCE DESCRIPTION: SEQ ID NO: 21:

```
Val  Arg  Val  Thr  His  Gln  Met  Leu  Phe  Asn  Thr  Asp  Gln  Val  Ile  Glu
1                   5                        10                       15

Val  Phe  Val  Ile  Gly  Val  Gly  Gly  Val  Gly  Gly  Ala  Leu  Leu  Glu  Gln
               20                       25                       30

Leu  Lys  Arg  Gln  Gln  Ser  Trp  Leu  Lys  Asn  Lys  His  Ile  Asp  Leu  Arg
          35                       40                       45

Val  Cys  Gly  Val  Ala  Asn  Ser  Lys  Ala  Leu  Leu  Thr  Glu  Val  His  Gly
     50                       55                       60

Leu  Asn  Leu  Glu  Asn  Trp  Gln  Glu  Glu  Leu  Ala  Gln  Ala  Lys  Glu  Pro
65                       70                       75                          80

Phe  Asn  Leu  Gly  Arg  Leu  Ile  Arg  Leu  Val  Lys  Glu  Tyr  His  Leu  Leu
                    85                       90                       95

Asn  Pro  Val  Ile  Val  Asn  Cys  Thr  Ser  Ser  Gln  Ala  Val  Ala  Asp  Gln
               100                      105                      110

Tyr  Ala  Asp  Phe  Leu  Arg  Glu  Gly  Phe  His  Val  Val  Thr  Pro  Asn  Lys
          115                      120                      125

Lys  Ala  Asn  Thr  Ser  Ser  Met  Asp  Tyr  Tyr  His  Gln  Leu  Arg  Tyr  Ala
130                      135                      140
```

```
Ala  Glu  Lys  Ser  Arg  Arg  Lys  Phe  Leu  Tyr  Asp  Ile  Asn  Val  Gly  Ala
145                     150                     155                     160

Gly  Leu  Pro  Val  Ile  Glu  Asn  Leu  Gln  Asn  Leu  Leu  Asn  Ala  Gly  Asp
                    165                     170                     175

Glu  Leu  Met  Lys  Phe  Ser  Gly  Ile  Leu  Ser  Gly  Ser  Leu  Ser  Tyr  Ile
               180                     185                     190

Phe  Gly  Lys  Leu  Asp  Glu  Gly  Met  Ser  Phe  Ser  Glu  Ala  Thr  Arg  Leu
          195                     200                     205

Ala  Arg  Glu  Met  Gly  Tyr  Thr  Glu  Pro  Asp  Pro  Arg  Asp  Asp  Leu  Ser
     210                     215                     220

Gly  Met  Asp  Val  Ala  Arg  Lys  Leu  Leu  Ile  Leu  Ala  Arg  Glu  Thr  Gly
225                     230                     235                     240

Arg  Glu  Leu  Glu  Leu  Ala  Asp  Ile  Glu  Ile  Glu  Pro  Val  Leu  Pro  Ala
                    245                     250                     255

Glu  Phe  Asn  Ala  Glu  Gly  Asp  Val  Ala  Ala  Phe  Met  Ala  Asn  Leu  Ser
               260                     265                     270

Gln  Leu  Asp  Asp  Leu  Phe  Ala  Ala  Arg  Val  Ala  Lys  Ala  Arg  Asp  Glu
          275                     280                     285

Gly  Lys  Val  Leu  Arg  Tyr  Val  Gly  Asn  Ile  Asp  Glu  Asp  Gly  Val  Cys
     290                     295                     300

Arg  Val  Lys  Ile  Ala  Glu  Val  Asp  Gly  Asn  Asp  Pro  Leu  Phe  Lys  Val
305                     310                     315                     320

Lys  Asn  Gly  Glu  Asn  Ala  Leu  Ala  Phe  Tyr  Ser  His  Tyr  Tyr  Gln  Pro
                    325                     330                     335

Leu  Pro  Leu  Val  Leu  Arg  Gly  Tyr  Gly  Ala  Gly  Asn  Asp  Val  Thr  Ala
               340                     345                     350

Ala  Gly  Val  Phe  Ala  Asp  Leu  Leu  Arg  Thr  Leu  Ser  Trp  Lys  Leu  Gly
          355                     360                     365

Val
```

( 2 ) INFORMATION FOR SEQ ID NO: 22:

( i ) SEQUENCE CHARACTERISTICS:
        ( A ) LENGTH: 366 amino acids
        ( B ) TYPE: amino acid
        ( D ) TOPOLOGY: linear ( x i ) SEQUENCE DESCRIPTION: SEQ ID NO: 22:

```
Ile  Gln  Gly  Leu  His  Gln  Ser  Val  Phe  Arg  Ala  Glu  Lys  Arg  Ile  Gly
1                   5                       10                      15

Leu  Val  Leu  Phe  Gly  Lys  Gly  Asn  Ile  Gly  Ser  Arg  Trp  Leu  Glu  Leu
               20                      25                      30

Phe  Ala  Arg  Glu  Gln  Ser  Thr  Leu  Ser  Ala  Arg  Thr  Gly  Phe  Glu  Phe
          35                      40                      45

Val  Leu  Ala  Gly  Val  Val  Asp  Ser  Arg  Arg  Ser  Leu  Leu  Ser  Tyr  Asp
     50                      55                      60

Gly  Leu  Asp  Ala  Ser  Arg  Ala  Leu  Ala  Phe  Phe  Asn  Asp  Glu  Ala  Val
65                      70                      75                      80

Glu  Gln  Asp  Glu  Glu  Ser  Leu  Phe  Leu  Trp  Met  Arg  Ala  His  Pro  Tyr
                    85                      90                      95

Asp  Asp  Leu  Val  Val  Leu  Asp  Val  Thr  Ala  Ser  Gln  Gln  Leu  Ala  Asp
               100                     105                     110

Gln  Tyr  Leu  Asp  Phe  Ala  Ser  His  Gly  Phe  His  Val  Ile  Ser  Ala  Asn
          115                     120                     125

Lys  Leu  Ala  Gly  Ala  Ser  Asp  Ser  Asn  Lys  Tyr  Arg  Gln  Ile  His  Asp
     130                     135                     140
```

```
Ala Phe Glu Lys Thr Gly Arg His Trp Leu Tyr Asn Ala Thr Val Gly
145                     150                 155                 160

Ala Gly Leu Pro Ile Asn His Thr Val Arg Asp Leu Ile Asp Ser Gly
                165                 170                 175

Asp Thr Ile Leu Ser Ile Ser Gly Ile Phe Ser Gly Thr Leu Ser Trp
            180                 185                 190

Leu Phe Leu Gln Phe Asp Gly Ser Val Pro Phe Thr Glu Leu Val Asp
        195                 200                 205

Gln Ala Trp Gln Gln Gly Leu Thr Glu Pro Asp Pro Arg Asp Asp Leu
    210                 215                 220

Ser Gly Lys Asp Val Ser Arg Lys Leu Val Ile Leu Ala Arg Glu Ala
225                 230                 235                 240

Gly Tyr Asn Ile Glu Pro Asp Gln Val Arg Val Glu Ser Leu Val Pro
                245                 250                 255

Ala His Cys Glu Gly Gly Ser Ile Asp His Phe Phe Glu Asn Gly Asp
            260                 265                 270

Glu Leu Asn Glu Gln Met Val Gln Arg Leu Glu Ala Ala Arg Glu Met
        275                 280                 285

Gly Leu Val Leu Arg Tyr Val Ala Arg Phe Asp Ala Asn Gly Lys Ala
    290                 295                 300

Arg Val Gly Val Glu Ala Val Arg Glu Asp His Pro Leu Ala Ser Leu
305                 310                 315                 320

Leu Pro Cys Asp Asn Val Phe Ala Ile Glu Ser Arg Trp Tyr Arg Asp
            325                 330                 335

Asn Pro Leu Val Ile Arg Gly Pro Gly Ala Gly Arg Asp Val Thr Ala
        340                 345                 350

Gly Ala Ile Gln Ser Asp Ile Asn Arg Leu Ala Gln Leu Leu
    355                 360                 365
```